United States Patent
Sekiya et al.

(10) Patent No.: US 11,295,487 B2
(45) Date of Patent: Apr. 5, 2022

(54) X-RAY CT APPARATUS, MEDICAL IMAGE PROCESSING APPARATUS, AND X-RAY CT SYSTEM

(71) Applicants: CANON MEDICAL SYSTEMS CORPORATION, Otawara (JP); National Cancer Center, Chuo-ku (JP)

(72) Inventors: Kotaro Sekiya, Bunkyo-ku (JP); Hirofumi Kuno, Nagareyama (JP); Takashi Hiyama, Kashiwa (JP); Tsubomi Hashizume, Sumida-ku (JP); So Tsushima, Nagareyama (JP); Shinsuke Tsukagoshi, Nasushiobara (JP)

(73) Assignees: CANON MEDICAL SYSTEMS CORPORATION, Otawara (JP); National Cancer Center, Chuo-ku (JP)

( * ) Notice: Subject to any disclaimer, the term of this patent is extended or adjusted under 35 U.S.C. 154(b) by 193 days.

(21) Appl. No.: 16/563,569

(22) Filed: Sep. 6, 2019

(65) Prior Publication Data
US 2020/0082579 A1    Mar. 12, 2020

(30) Foreign Application Priority Data

Sep. 7, 2018   (JP) .............................. JP2018-167581
Sep. 6, 2019   (JP) .............................. JP2019-162621

(51) Int. Cl.
  *G06T 11/00*   (2006.01)
  *G06T 7/00*    (2017.01)
  *A61B 6/00*    (2006.01)

(52) U.S. Cl.
  CPC ............ *G06T 11/005* (2013.01); *A61B 6/482* (2013.01); *G06T 7/0012* (2013.01); *G06T 2207/10081* (2013.01); *G06T 2211/408* (2013.01)

(58) Field of Classification Search
None
See application file for complete search history.

(56) References Cited

U.S. PATENT DOCUMENTS

2006/0215889 A1* 9/2006 Omi ....................... A61B 6/507
                                                              382/128
2009/0262997 A1* 10/2009 Zou ....................... A61B 6/583
                                                              382/131

(Continued)

FOREIGN PATENT DOCUMENTS

| JP | 2009-261942 A | 11/2009 |
| JP | 2011-110245 A | 6/2011 |
| WO | WO2004/089218 A1 | 10/2004 |

OTHER PUBLICATIONS

Extended European Search Report dated Feb. 12, 2020, in Patent Application No. 19195978.2, 15 pages.

(Continued)

*Primary Examiner* — Hoon K Song
(74) *Attorney, Agent, or Firm* — Oblon, McClelland, Maier & Neustadt, L.L.P.

(57) ABSTRACT

An X-ray CT apparatus according to an embodiment includes processing circuitry. The processing circuitry acquires a first data set corresponding to first X-ray energy and a second data set corresponding to second X-ray energy different from the first X-ray energy, with respect to a region including a part of a subject by performing scanning using X-rays. The processing circuitry generates a scatter diagram representing a contained amount of each of reference materials at each of positions in the region on the basis of the first data set and the second data set. The processing circuitry sets weights for at least a part of the scatter diagram. The processing circuitry generates an analysis image based on the contained amounts and the weights.

24 Claims, 12 Drawing Sheets

(56) References Cited

U.S. PATENT DOCUMENTS

| | | | |
|---|---|---|---|
| 2015/0161787 A1* | 6/2015 | Li | A61B 6/5217 |
| | | | 382/122 |
| 2016/0213344 A1* | 7/2016 | Yi | A61B 6/5282 |
| 2017/0018099 A1* | 1/2017 | Heukensfeldt Jansen | |
| | | | G06T 11/005 |
| 2018/0146945 A1* | 5/2018 | Hofmann | A61B 6/032 |
| 2019/0162679 A1* | 5/2019 | Yamakawa | G01N 23/087 |

OTHER PUBLICATIONS

Petrongolo, M. and Zhu, L., "Noise Suppression for Dual-Energy CT Through Entropy Minimization", IEEE Transactions on Medical Imaging, XP011588709, vol. 34, No. 11, Nov. 2015, pp. 2286-2297.

Son, J. Y. et al., "Quantitative CT analysis of pulmonary ground-glass opacity nodules for distinguishing invasive adenocarcinoma from non-invasive or minimally invasive adenocarcinoma: the added value of using iodine mapping", European Radiology, XP035874155, vol. 26, No. 1, May 17, 2015, pp. 43-54.

\* cited by examiner

FIG.11
| | | | | |
|---|---|---|---|---|
| (1, 1) | (1, 2) | (1, 3) | ... | |
| (2, 1) | | | | |
| (3, 1) | | | | |
| ⋮ | | | | |
| | IODINE (WATER) | WATER (IODINE) |
|---|---|---|
| (1, 1) | 10 | 815 |
| (1, 2) | 13 | 822 |
| (1, 3) | 11 | 811 |
| (1, 4) | 20 | 950 |
| (1, 5) | 60 | 1022 |
| ⋮ | ⋮ | ⋮ |
| (2, 1) | 13 | 772 |
| (2, 2) | 6 | 515 |
| (2, 3) | 13 | 822 |
| (2, 4) | 255 | 1506 |
| ⋮ | ⋮ | ⋮ |
| GROUP A | GROUP B | GROUP C | ... |
|---|---|---|---|
| 10:815 | 60:1022 | 255:1506 | |
| 13:822 | . | . | |
| 11:811 | . | . | |
| . | . | . | |
| . | . | . | |
| . | . | . | |
| 13:772 | . | . | |
| 13:822 | . | . | |
| . | . | . | |
| . | . | . | |
| . | . | . | |
| . | . | . | |

X-RAY CT APPARATUS, MEDICAL IMAGE PROCESSING APPARATUS, AND X-RAY CT SYSTEM

CROSS-REFERENCE TO RELATED APPLICATIONS

This application is based upon and claims the benefit of priority from Japanese Patent Application No. 2018-167581, filed on Sep. 7, 2018 and Japanese Patent Application No. 2019-162621, filed on Sep. 6, 2019; the entire contents of which are incorporated herein by reference.

FIELD

Embodiments described herein relate generally to an X-ray CT apparatus, a medical image processing apparatus, and an X-ray CT system.

BACKGROUND

Conventionally, a technique of causing an X-ray computed tomography apparatus to acquire images by performing imaging at a plurality of different tube voltages has been known. For example, in dual-energy (DE) acquisition using two different tube voltages, a technique of decomposing two pieces of projection data that are obtained at the two different tube voltages into two pieces of projection data (line integral data) for two respective reference materials that are set in advance, and reconstructing images (reference material images) based on abundance ratios of the reference materials from the two respective pieces of decomposed data has been known. In this technique, it is possible to obtain various images, such as a monochromatic X-ray image, a density image, and an effective atomic number image, by performing a weighted calculation process using the two reference material images.

BRIEF DESCRIPTION OF THE DRAWINGS

FIG. 11 is a schematic diagram for explaining a process performed by an analysis function according to a fifth embodiment.

DETAILED DESCRIPTION

An X-ray CT apparatus includes processing circuitry. The processing circuitry is configured to acquire a first data set corresponding to first X-ray energy and a second data set corresponding to second X-ray energy different from the first X-ray energy, with respect to a region including a part of a subject by performing scanning using X-rays. The processing circuitry is configured to generate a scatter diagram representing a contained amount of each of reference materials at each of positions in the region on the basis of the first data set and the second data set. The processing circuitry is configured to set weights for at least a part of the scatter diagram. The processing circuitry is configured to generate an analysis image based on the contained amounts and the weights.

Embodiments of an X-ray CT apparatus, a medical image processing apparatus, and an X-ray CT system will be described in detail below with reference to the drawings. The X-ray CT apparatus, the medical image processing apparatus, and the X-ray CT system according to the present disclosure are not limited to the embodiments described below.

First Embodiment

First, a first embodiment will be described. In the first embodiment, an example will be described in which a technique disclosed in the present disclosure is applied to an X-ray CT apparatus. In the following, a medical image processing system including the X-ray CT apparatus will be described as an example.

Figure 1:
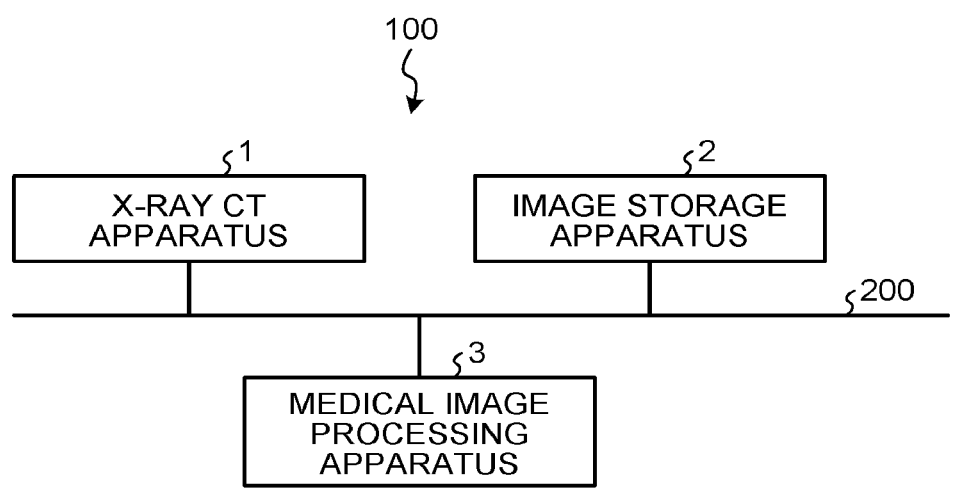
FIG. 1 is a diagram illustrating an example of a configuration of a medical image processing system according to a first embodiment.

FIG. 1 is a diagram illustrating a configuration example of the medical image processing system according to the first embodiment. As illustrated in FIG. 1, a medical image processing system 100 according to the first embodiment includes an X-ray computed tomography (CT) apparatus 1, an image storage apparatus 2, and a medical image processing apparatus 3, all of which are connected to one another via a network 200. The example illustrated in FIG. 1 is one example, and it may be possible to connect various other apparatuses (for example, a terminal device and the like) to the network 200.

For example, as illustrated in FIG. 1, the X-ray CT apparatus 1 according to the first embodiment is connected to the image storage apparatus 2 and the medical image processing apparatus 3 via the network 200. The medical image processing system 100 may further be connected to other medical image diagnostic apparatuses, such as an MRI apparatus, an ultrasonic diagnostic apparatus, and a positron emission tomography (PET) apparatus, or further be connected to a terminal device and the like via the network 200. Furthermore, the network 200 may be configured with a closed local network in a hospital or configured with a network via the Internet.

The image storage apparatus 2 stores therein image data collected by various medical image diagnostic apparatuses. For example, the image storage apparatus 2 is realized by a computer device, such as a server device. In the present embodiment, the image storage apparatus 2 collects projection data and CT image data (volume data) from the X-ray CT apparatus 1 via the network 200, and stores the collected projection data and the collected CT image data in memory circuitry that is arranged inside or outside of the apparatus.

The medical image processing apparatus 3 collects image data from various medical image diagnostic apparatuses via the network 200 and processes the collected image data. For example, the medical image processing apparatus 3 is realized by a computer device, such as a workstation. In the present embodiment, the medical image processing apparatus 3 collects projection data and CT image data from the X-ray CT apparatus 1 or the image storage apparatus 2 via the network 200, and performs various kinds of image processing on the collected projection data and the collected CT image data. The medical image processing apparatus 3 displays, on a display or the like, the CT image data before or after image processing is performed on the CT image data.

The X-ray CT apparatus 1 acquires CT image data on a subject. Specifically, the X-ray CT apparatus 1 moves an X-ray tube and an X-ray detector in a rotating manner substantially around the subject, detects X-rays that have transmitted through the subject, and acquires projection data. Here, the X-ray CT apparatus 1 captures images at a plurality of different kinds of tube voltages, and acquires a plurality of kinds of projection data sets. For example, the X-ray CT apparatus 1 acquires two projection data sets for a single imaging target region by performing dual-energy (DE) acquisition using two different kinds of tube voltages. Then, the X-ray CT apparatus 1 generates CT image data based on the acquired projection data.

Figure 2:
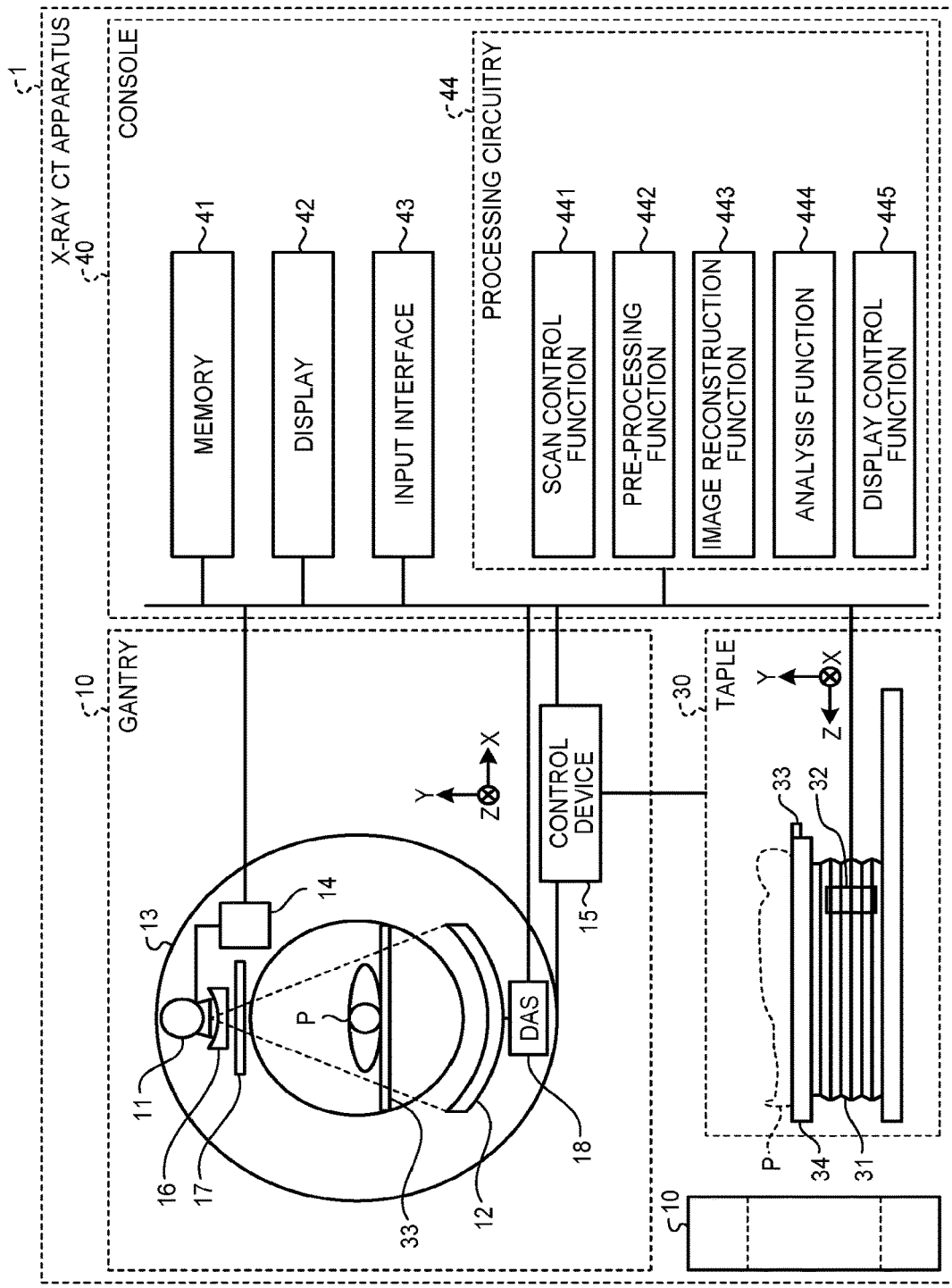
FIG. 2 is a block diagram illustrating a configuration example of an X-ray CT apparatus according to the first embodiment.

FIG. 2 is a diagram illustrating a configuration example of the X-ray CT apparatus 1 according to the first embodiment. As illustrated in FIG. 2, the X-ray CT apparatus 1 according to the first embodiment includes a gantry 10, a table 30, and a console 40.

Here, in FIG. 2, a rotation axis of a rotary frame 13 in a non-tilted state or a longitudinal direction of a tabletop 33 of the table 30 is assumed as a Z-axis direction. Further, an axial direction orthogonal to the Z-axis direction and horizontal with respect to a floor surface is assumed as an X-axis direction. Furthermore, an axial direction orthogonal to the Z-axis direction and normal to the floor surface is assumed as a Y-axis direction. While the gantry 10 is viewed from a plurality of directions for the sake of explanation in FIG. 2, the X-ray CT apparatus 1 includes the single gantry 10.

The gantry 10 includes an X-ray tube 11, an X-ray detector 12, the rotary frame 13, an X-ray high-voltage generator 14, a control device 15, a wedge 16, a collimator 17, and a data acquisition system (DAS) 18.

The X-ray tube 11 is a vacuum tube that includes a cathode (filament) for generating thermal electrons and an anode (target) for generating X-rays in response to collision of the thermal electrons. The X-ray tube 11 emits thermal electrons from the cathode to the anode by receiving a high voltage applied from the X-ray high-voltage generator 14, and generates X-rays for irradiating the subject P. For example, the X-ray tube 11 includes a rotary anode x-ray tube that generates X-rays by irradiating the rotating anode with thermal electrons.

The X-ray detector 12 includes a plurality of detection elements for detecting X-rays. Each of the detection elements in the X-ray detector 12 detects X-rays that have been emitted from the X-ray tube 11 and transmitted through a subject P, and outputs a signal corresponding to the amount of detected X-rays to the DAS 18. The X-ray detector 12 includes, for example, a plurality of detection element rows, in which a plurality of detection elements are arranged in a channel direction along a single circular arc centered at a focal point of the X-ray tube 11. The X-ray detector 12 is configured such that, for example, the plurality of detection element rows, in each of which the plurality of detection elements are arranged in the channel direction, are arranged in a row direction (slice direction).

For example, the X-ray detector 12 is an indirect conversion type detector that includes a grid, a scintillator array, and an optical sensor array. The scintillator array includes a plurality of scintillators. Each of the scintillators includes a scintillator crystal that outputs light with a certain amount of photons corresponding to an amount of incident X-rays. The grid is arranged on an X-ray incident surface of the scintillator array and includes an X-ray shielding plate that absorbs scattered X-rays. Meanwhile, the grid may also be referred to as a collimator (a one-dimensional collimator or a two-dimensional collimator). The optical sensor array has a function to perform conversion to electrical signals corresponding to the amount of light from the scintillators, and includes, for example, an optical sensor, such as a photodiode. Meanwhile, the X-ray detector 12 may be a direct conversion type detector that includes a semiconductor element for converting incident X-rays into electrical signals.

The rotary frame 13 is an annular frame that supports the X-ray tube 11 and the X-ray detector 12 in a facing manner and is caused to rotate the X-ray tube 11 and the X-ray detector 12 by the control device 15. For example, the rotary frame 13 is a casting made of aluminum. Meanwhile, the rotary frame 13 is able to further support the X-ray high-voltage generator 14, the wedge 16, the collimator 17, the DAS 18, and the like, in addition to the X-ray tube 11 and the X-ray detector 12. Furthermore, the rotary frame 13 is able to further support various components that are not illustrated in FIG. 2.

The X-ray high-voltage generator 14 includes electrical circuitries, such as a transformer (Xfmr) and a rectifier, a high-voltage generator that generates a high voltage to be applied to the X-ray tube 11, and an X-ray control device that controls an output voltage in accordance with X-rays generated by the X-ray tube 11. The high-voltage generator may be of a transformer system or an inverter system. The X-ray high-voltage generator 14 may be mounted on the rotary frame 13 or on a fixed frame (not illustrated).

The control device 15 includes processing circuitry including a central processing unit (CPU) and the like, and driving mechanisms, such as a motor and an actuator. The control device 15 receives an input signal from an input interface 43, and controls operation of the gantry 10 and the table 30. For example, the control device 15 controls rotation of the rotary frame 13, tilt of the gantry 10, operation of the table 30 and the tabletop 33, and the like. As one example, as control of tilting the gantry 10, the control device 15 rotates the rotary frame 13 about an axis parallel to the X-axis direction on the basis of input inclination angle (tilt angle) information. The control device 15 may be mounted on the gantry 10 or the console 40.

The wedge 16 is a filter for adjusting the amount of X-rays emitted from the X-ray tube 11. Specifically, the wedge 16 is a filter that transmits and attenuates the X-rays emitted from the X-ray tube 11 such that X-rays applied from the X-ray tube 11 to the subject P are distributed in a predetermined manner. For example, the wedge 16 may be a wedge filter or a bow-tie filter, and is obtained by processing aluminum or the like so as to have a predetermined target angle and a predetermined thickness.

The collimator 17 is a lead plate or the like for narrowing down an irradiation range of the X-rays transmitted through the wedge 16, and includes a slit formed by a combination of a plurality of lead plates. The collimator 17 may also be referred to as an X-ray diaphragm. While FIG. 2 illustrates a case in which the wedge 16 is arranged between the X-ray tube 11 and the collimator 17, it may be possible to arrange the collimator 17 between the X-ray tube 11 and the wedge 16. In this case, the wedge 16 transmits and attenuates X-rays which are emitted from the X-ray tube 11 and for which an irradiation range is limited by the collimator 17.

The DAS 18 acquires signals of X-ray detected by each of the detection elements included in the X-ray detector 12. For example, the DAS 18 includes an amplifier that performs an amplification process on electrical signals output from each of the detection elements and an analog-to-digital (A/D) converter that converts the electrical signals into digital signals, and generates detection data. The DAS 18 is realized by, for example, a processor.

The data generated by the DAS 18 is transmitted from a transmitter, which is arranged on the rotary frame 13 and includes a light emitting diode (LED), to a receiver, which is arranged on a non-rotary portion of the gantry 10 (for example, a fixed frame or the like (not illustrated in FIG. 1)) and includes a photodiode, through optical communication, and is further transferred to the console 40. Here, the non-rotary portion is, for example, a fixed frame or the like that supports the rotary frame 13 such that the rotary frame 13 can rotate. Meanwhile, a method of transmission from the rotary frame 13 to the non-rotary portion of the gantry 10 is not limited to the optical communication, but it may be possible to adopt any contactless data transmission method or any contact data transmission method.

The table 30 is a device for placing and moving the subject P as an imaging target, and includes a pedestal 31, table driving circuitry 32, the tabletop 33, and a support frame 34. The pedestal 31 is a casing that supports the support frame 34 such that the support frame 34 can move in a vertical direction. The table driving circuitry 32 is a driving mechanism that moves the tabletop 33 on which the subject P is placed in a long-axis direction of the tabletop 33, and includes a motor, an actuator, and the like. The tabletop 33 arranged on an upper surface of the support frame 34 is a plate on which the subject P is placed. Meanwhile, the table driving circuitry 32 may move the support frame 34 in the long-axis direction of the tabletop 33 in addition to the tabletop 33.

The console 40 includes a memory 41, a display 42, the input interface 43, and processing circuitry 44. While the console 40 is separated from the gantry 10 in the example described below, the gantry 10 may include the console 40 or a part of components of the console 40.

The memory 41 is realized by, for example, a semiconductor memory element, such as a random access memory (RAM) or a flash memory, a hard disk, an optical disk, or the like. The memory 41 stores therein, for example, projection data and CT image data. Further, the memory 41 stores therein information on a region of interest. The region of interest will be described in detail later. Furthermore, for example, the memory 41 stores therein a program for causing the circuitries included in the X-ray CT apparatus 1 to realize certain functions. The memory 41 may be realized by a server group (cloud) that is connected to the X-ray CT apparatus 1 via a network.

The display 42 displays various kinds of information. For example, the display 42 displays various images generated by the processing circuitry 44 and a graphical user interface (GUI) for receiving various kinds of operation from an operator. For example, the display 42 may be a liquid crystal display or a cathode ray tube (CRT) display. The display 42 may be of a desktop type or may be configured with a tablet terminal or the like capable of performing wireless communication with a main body of the console 40.

The input interface 43 receives various kinds of input operation from the operator, converts the received input operation into an electrical signal, and outputs the electrical signal to the processing circuitry 44. For example, the input interface 43 receives, from the operator, input operation of performing designation operation on information displayed by the display 42. The designation operation will be described later. Further, for example, the input interface 43 receives, from the operator, input operation on a reconstruction condition for reconstructing CT image data, an image processing condition for generating a post-processing image from the CT image data, or the like.

For example, the input interface 43 is realized by a mouse, a keyboard, a trackball, a switch, a button, a joystick, a touch-pad for performing input operation by touching an operation screen, a touch screen in which a display screen and a touch-pad are integrated, contactless input circuitry using an optical sensor, voice input circuitry, or the like. The input interface 43 may be mounted on the gantry 10. Further, the input interface 43 may be configured with a tablet terminal or the like capable of performing wireless communication with the main body of the console 40. Furthermore, the input interface 43 is not limited to a device that includes a physical operation component, such as a mouse or a keyboard. For example, examples of the input interface 43 include electrical signal processing circuitry that receives an electrical signal corresponding to input operation from an external input device that is arranged separately from the console 40, and outputs the electrical signal to the processing circuitry 44.

The processing circuitry 44 controls the entire operation of the X-ray CT apparatus 1. For example, the processing circuitry 44 executes a scan control function 441, a preprocessing function 442, an image reconstruction function 443, an analysis function 444, and a display control function 445.

In the X-ray CT apparatus 1 illustrated in FIG. 2, each of the processing functions is stored in the memory 41 in the form of a program that can be executed by a computer. The processing circuitry 44 is a processor that implements functions corresponding to each of the programs by reading the programs from the memory 41 and executing the programs. In other words, the processing circuitry 44 that has read each of the programs has functions corresponding to the read programs.

While FIG. 2 illustrates a case in which each of the processing functions of the scan control function 441, the pre-processing function 442, the image reconstruction function 443, the analysis function 444, and the display control function 445 is realized by the single processing circuitry 44, embodiments are not limited to this example. For example, the processing circuitry 44 may be configured by a combination of a plurality of independent processors, and implement each of the processing functions by causing each of the processors to execute each of the programs. Further, each of the processing functions included in the processing circuitry 44 may be appropriately distributed or integrated in a single or a plurality of processing circuitries.

The entire configuration of the X-ray CT apparatus 1 according to the present embodiment has been described above. With this configuration, the X-ray CT apparatus 1 according to the present embodiment provides a CT image in which tissue resolution is improved. Specifically, the X-ray CT apparatus 1 generates a CT image in which contrast is emphasized for each of tissues, by using projection data that is acquired by capturing images at a plurality of different kinds of tube voltages or by using CT image data that is reconstructed from the projection data, with use of various functions implemented by the processing circuitry 44.

For example, in a CT image that is captured by plain CT scan in which a contrast agent is not used, CT values of soft tissues, such as a brain, a tumor, and a muscle, are similar to one another, so that it may be difficult to clearly distinguish among the tissues in the CT image on the basis of a difference in the contrast based on the CT values. Therefore, in the X-ray CT apparatus according to the present disclosure, reference material images that are obtained by capturing images at a plurality of different tube voltages are analyzed, a mixture ratio of reference materials is obtained for each of pixels, and a CT image in which the contrast is emphasized for each of tissues based on the acquired mixture ratio is generated.

In the present embodiment, "imaging at a plurality of different tube voltages" includes "Dual-Energy imaging" at two different tube voltages and "Multi-Energy imaging" at three or more different tube voltages. In the case of "Dual-Energy imaging", it may be possible to use any of the following four imaging methods.

For example, a first method is a "Slow-kV switching method (double rotation method)", in which imaging is performed at a first tube voltage using a single X-ray tube and thereafter imaging is performed at a second tube voltage that is different from the first tube voltage. Further, for example, a second method is a "Fast-kV switching method (high-speed switching method)", in which imaging is performed while rapidly switching the tube voltage of the X-ray tube on a view-by-view basis during rotation (scanning). In this case, a data acquisition device acquires data in synchronization with switching of the tube voltage and acquires pieces of data at different tube voltages in single scan. Furthermore, for example, a third method is a "Dual Source method (dual tube method)", in which two X-ray tubes instead of a single X-ray tube are mounted and imaging is performed at different tube voltages using the two X-ray tubes. Moreover, for example, a fourth method is a "multi-layer detector method", in which X-ray detectors having a multilayered structure is used. For example, if an X-ray detector having a double-layered structure (a detector in a shallow layer and a detector in a deep layer) is used, the detector in the shallow layer detects low-energy X-rays and the detector in the deep layer detects high-energy X-rays that have passed through the detector in the shallow layer.

Each of the functions will be described in detail below. In the following, a case will be described in which "Dual-Energy imaging" is performed using the "Fast-kV switching method" to capture images at two different tube voltages and a CT image in which contrast is enhanced for each of tissues is generated.

The scan control function 441 controls scanning on the basis of input operation that is received from the operator via the input interface 43. Specifically, the scan control function 441 transmits a control signal to the X-ray high-voltage generator 14 on the basis of the input operation, and controls an output voltage from the high-voltage generator. Further, the scan control function 441 transmits a control signal to the DAS 18, and controls data acquisition performed by the DAS 18.

Here, the scan control function 441 acquires a first data set corresponding to first X-ray energy and a second data set corresponding to second X-ray energy different from the first X-ray energy, with respect to a region including a part of the subject by performing scanning using X-rays. For example, the scan control function 441 controls the "Dual-Energy imaging" using the "Fast-kV switching method".

In this case, the scan control function 441 transmits a control signal for switching between a high voltage and a low voltage to the X-ray high-voltage generator 14, and controls application of the high voltage and the low voltage from the X-ray high-voltage generator 14 to the X-ray tube 11. Further, the scan control function 441 transmits a control signal to the DAS 18 to distinguish whether the detected detection data is obtained by X-ray irradiation at the high voltage or X-ray irradiation at the low voltage.

The pre-processing function 442 performs a correction process, such as a logarithmic transformation process, offset correction, sensitivity correction, or beam hardening correction, on the X-ray detection data transmitted from the DAS 18, and generates projection data. Meanwhile, data (detection data) that is not subjected to the pre-processing and data subjected to the pre-processing may be collectively referred to as the projection data. For example, the pre-processing function 442 generates a projection data set (hereinafter, described as a high-energy projection data set) from the detection data obtained at the first tube voltage (for example, a high voltage). Further, the pre-processing function 442 generates a projection data set (hereinafter, described as a low-energy projection data set) from the detection data obtained at the second tube voltage (for example, a low voltage).

Furthermore, the pre-processing function 442 separates two or more predetermined reference materials (water, iodine, calcium, hydroxyapatite, fat, and the like) that are present in an imaging target region by using the two kinds of projection data sets. Then, the pre-processing function 442 generates two or more kinds of monochromatic X-ray projection data sets respectively corresponding to the two or more reference materials. For example, the pre-processing function 442 generates a monochromatic X-ray projection data set for each of water and iodine from the high-energy projection data set and the low-energy projection data set. Meanwhile, the projection data sets generated by the pre-processing function 442 are stored in the memory 41.

The image reconstruction function 443 generates various images from the projection data sets stored in the memory 41, and stores the generated images in the memory 41. For example, the image reconstruction function 443 reconstructs CT image data by reconstructing the projection data by various reconstruction methods (for example, a back projection method, such as a filtered back projection (FBP), successive approximation, or the like), and stores the reconstructed CT image data in the memory 41. Further, the image reconstruction function 443 generates a CT image, such as an MPR image, from the CT image data by performing various kinds of image processing, and stores the generated CT image in the memory 41.

For example, the image reconstruction function 443 reads the monochromatic X-ray projection data sets that correspond to the reference materials and that are stored in the memory 41, and reconstructs reference material image data (reference material enhanced image data). As one example, the image reconstruction function 443 reconstructs reference material image data on a water component on the basis of the projection data set in which the water component is enhanced, and reconstructs reference material image data on an iodine component on the basis of the projection data set in which the iodine component is enhanced. Further, the image reconstruction function 443 performs image processing on each of the reference material image data on the water component and the reference material image data on the iodine component, and generates a reference material image of the water component and a reference material image of the iodine component. Furthermore, the image reconstruction function 443 is able to generate various images, such as a monochromatic X-ray image, a density image, or an effective atomic number image, at predetermined energy, by performing a weighted calculation process using the two pieces of reference material image data.

Moreover, for example, the image reconstruction function 443 reads the high-energy projection data set and the low-energy projection data set stored in the memory 41, and reconstructs CT image data from each of the projection data sets. Then, the image reconstruction function 443 is able to generate a multicolor X-ray image corresponding to the high energy and a multicolor X-ray image corresponding to the low energy from the CT image data.

The analysis function 444 performs various analysis processes on the CT image data and the CT image stored in the memory 41. For example, the analysis function 444 generates a scatter diagram that represents a contained amount of each of the reference materials at each of positions in a region on the basis of the first data set (for example, the high-energy projection data set) and the second data set (for example, the low-energy projection data set), sets weights for at least a part of the scatter diagram, and generates an analysis image based on only the contained amounts and the weights.

In this case, the analysis function 444 first estimates abundance ratios among the plurality of reference materials for each of pixels on the basis of the first data set and the second data set. For example, the analysis function 444 estimates abundance ratios of one of water and iodine to the other one of water and iodine for each of the pixels on the basis of pixel values of the multicolor X-ray image corresponding to the high energy and the multicolor X-ray image corresponding to the low energy, where the multicolor X-ray images are generated by the image reconstruction function 443. That is, the analysis function 444 estimates each of the abundance ratio of iodine to water and the abundance ratio of water to iodine for each of the pixels of a region that is captured by the Dual Energy imaging.

Then, the analysis function 444 generates a scatter diagram centering on the estimated abundance ratios, sets a weight for each of positions in the generated scatter diagram, and generates an analysis image in which a luminance value of a pixel corresponding to each of the positions is converted to a luminance value that reflects the weight. That is, the analysis function 444 generates a CT image in which tissue resolution is improved, by using the scatter diagram centering on the abundance ratios of the reference materials. Meanwhile, generation of the analysis image will be described in detail later.

Figure 3:
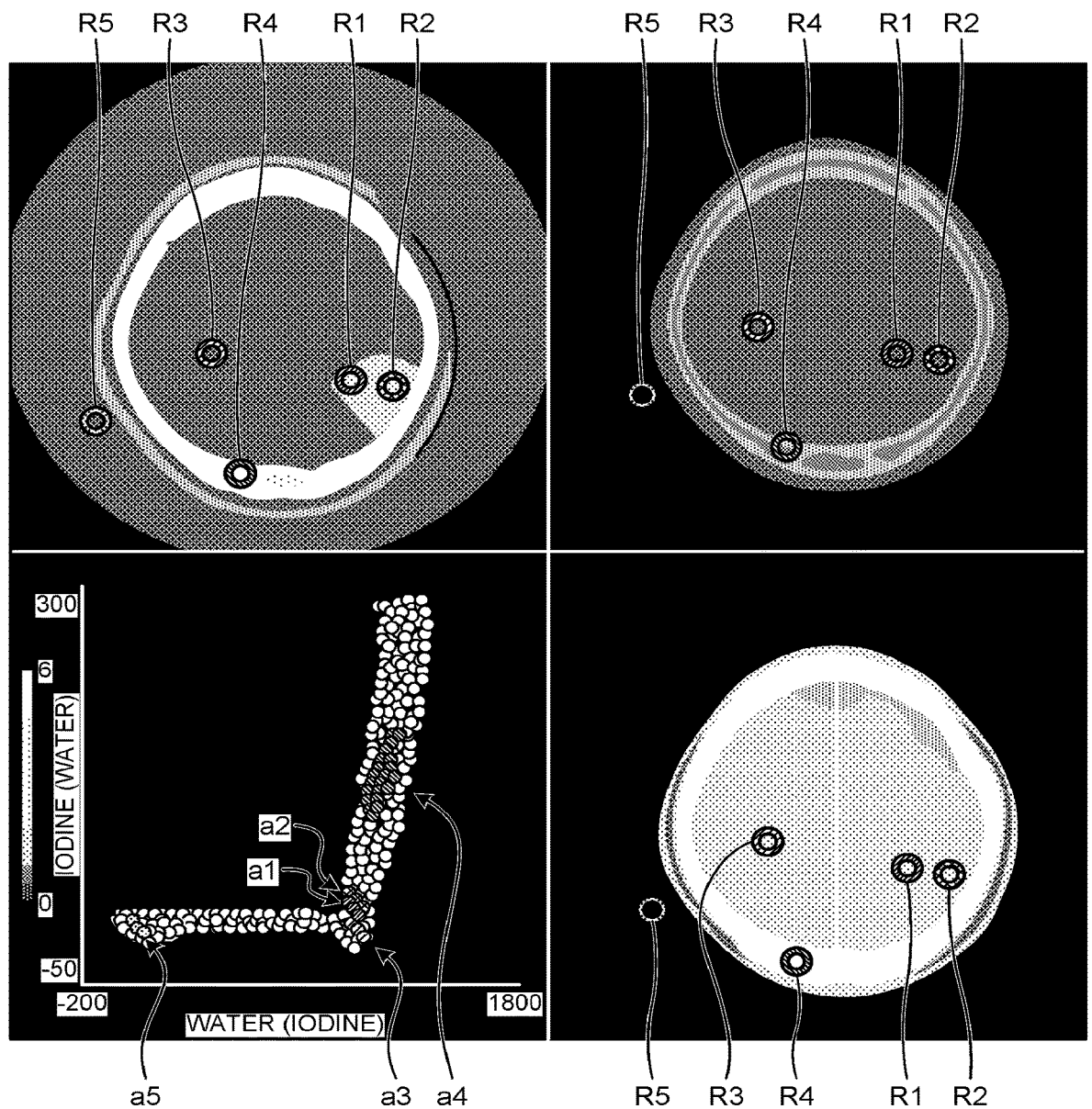
FIG. 3 is a diagram illustrating an example of display information according to the first embodiment.

The display control function 445 displays the CT image generated by the image reconstruction function 443 and displays the scatter diagram, the analysis image, and the like generated by the analysis function 444, on the display 42. FIG. 3 is a diagram illustrating an example of display information according to the first embodiment. FIG. 3 illustrates the reference material image of the iodine component, the reference material image of the water component, the monochromatic X-ray image, and the scatter diagram. For example, as illustrated in FIG. 3, the display control function 445 causes the display 42 to display the reference material image of the iodine component (upper left in the figure), the reference material image of the water component (upper right in the figure), the monochromatic X-ray image (lower right in the figure), and the scatter diagram (lower left in the figure), with respect to a single cross-section of a brain.

Here, the scatter diagram generated by the analysis function 444 is a graph as illustrated in the lower left in FIG. 3 for example, in which the vertical axis represents the abundance ratio of iodine to water and the horizontal axis represents the abundance ratio of water to iodine. In this case, for example, the analysis function 444 generates the scatter diagram by plotting points representing the respective pixels in the graph, on the basis of the abundance ratio of iodine to water and the abundance ratio of water to iodine that are estimated for each of the pixels. That is, the analysis function 444 generates the scatter diagram that represents a mixture ratio of water and iodine by the coordinate in the graph for each of the pixels.

Here, the scatter diagram illustrated in FIG. 3 is represented in a two-dimensional manner, but in reality, includes three-dimensional information content. Specifically, the scatter diagram illustrated in FIG. 3 represents the mixture ratio of water and iodine for each of the pixels. Therefore, in a case of an identical tissue (identical substance), the mixture ratio of water and iodine becomes substantially identical, and pixels included in the identical tissue are plotted on substantially the same coordinate on the scatter diagram. That is, the scatter diagram illustrated in FIG. 3 includes a plurality of points that overlap with one another in a depth direction, and includes the three-dimensional information content on the vertical axis, the horizontal axis, and the depth direction.

Further, a positional relationship of the scatter diagram illustrated in FIG. 3 is associated with those of the reference material image of the iodine component, the reference material image of the water component, and the monochromatic X-ray image that are displayed by the display control function 445. That is, positions of pixels in each of the images are associated with positions of corresponding pixels in the scatter diagram; for example, positions of pixel groups included in a region R1 in each of the images correspond to point groups indicated by an arrow a1 in the scatter diagram. For example, if the operator, such as a doctor, sets the region R1 in any of the images via the input interface 43, the display control function 445 is able to display the region R1 at a corresponding position in each of the other images, and display the point groups indicated by the arrow a1 in a different color.

Similarly, as illustrated in FIG. 3, the display control function 445 displays point groups that are included in the scatter diagram and that correspond to respective pixel groups included in a region R2 to a region R5 in each of the images, in different colors as indicated by an arrow a2 to an arrow a5. Here, the display control function 445 displays a region and point groups associated with the region using the same color, and uses different colors among the region R1 to the region R5 (the arrow a1 to the arrow a5), so that it is possible to display the regions and the point groups in a distinguishing manner.

As described above, the X-ray CT apparatus 1 displays the CT image in which the tissue resolution is improved by using the scatter diagram. Here, the scatter diagram generated by the analysis function 444 represents the mixture ratio of the reference materials by the coordinates in the graph. Therefore, it is assumed that the point groups representing the pixels of the identical tissue are plotted at substantially the same position on the scatter diagram. However, it is often the case that, in an actual scatter diagram, even the positions of the pixels included in the identical tissue are distributed due to the influence of noise or the like as illustrated in FIG. 3.

Therefore, in the present disclosure, weights are set in accordance with the positions on the scatter diagram, and the set weights are reflected in the luminance values of the CT image, so that a CT image in which contrast of each of tissues is enhanced and the tissue resolution is improved is provided even if the CT image is captured by plain CT scan.

Figure 4:
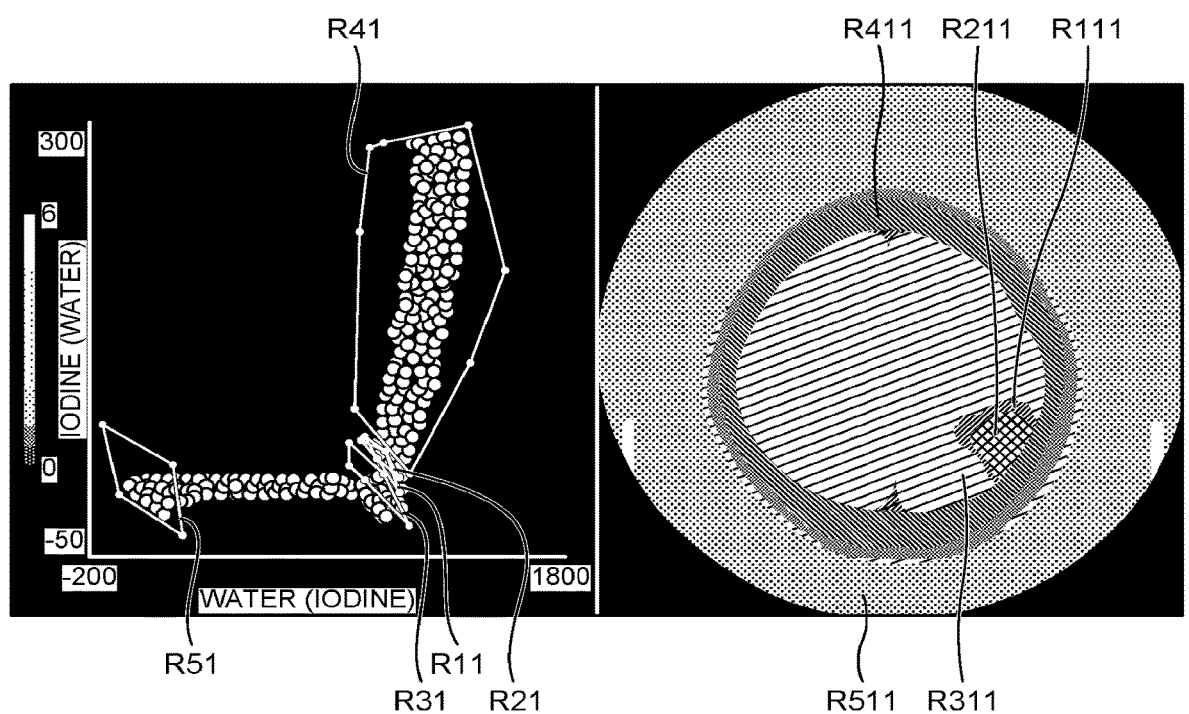
FIG. 4 is a diagram for explaining designation of regions of interest on a scatter diagram according to the first embodiment.

To realize the process as described above, the analysis function 444 first identifies, in the scatter diagram, an approximate position of a target tissue for which the contrast is to be enhanced. For example, the analysis function 444 receives designation operation of designating a region of interest indicating a position of the target tissue via the input interface 43, and identifies an approximate position of the target tissue on the scatter diagram. FIG. 4 is a diagram for explaining designation of regions of interest on the scatter diagram according to the first embodiment. In FIG. 4, the scatter diagram is illustrated on the left side, and the monochromatic X-ray image is illustrated on the right side.

For example, as illustrated in FIG. 4, when the display control function 445 causes the display 42 to display the scatter diagram and the monochromatic X-ray image, the operator, such as a doctor, sets regions, such as a region of interest R11 to a region of interest R51, on the scatter diagram via the input interface 43. Here, the operator may set the regions of interest by directly setting each of the regions of interest on the scatter diagram or setting each of the regions of interest by designating positions on the monochromatic X-ray image.

For example, if the operator directly sets the regions of interest on the scatter diagram, the display control function 445 displays, on the monochromatic X-ray image, pixel groups corresponding to point groups included in the set regions of interest, in an enhanced manner. As one example, if the operator directly sets the region of interest R11 on the scatter diagram, the display control function 445 displays, as illustrated in the diagram on the right side in FIG. 4, a region R111, which is a region of pixel groups corresponding to point groups included in the region of interest R11, in a different color in the monochromatic X-ray image. Therefore, the operator is able to set the region of interest while checking, on the image, a region corresponding to the region of interest designated on the scatter diagram.

Then, if a plurality of target tissues for which contrast is to be enhanced is present, as illustrated in FIG. 4 for example, the operator sets the region of interest R21 to the region of interest R51 on the scatter diagram. Even in this case, similarly to the above, the display control function 445 displays a region R211 to a region R511 corresponding to the region of interest R21 to the region of interest R51 in different colors on the image, so that it is possible to check, on the image, the regions corresponding to the regions of interest designated on the scatter diagram.

Further, if the operator sets a region on the image, the display control function 445 displays point groups corresponding to pixel groups included in the set region, in an enhanced manner on the scatter diagram. As one example, if the operator sets the region R111 on the monochromatic X-ray image, the display control function 445 displays, on the scatter diagram, point groups corresponding to pixel groups included in the region R111 in a different color. Therefore, the operator is able to recognize, on the scatter diagram, positions of the point groups corresponding to the pixel groups of the target tissue. The operator is able to set, on the scatter diagram, the region of interest R11 corresponding to the region R111 by setting, via the input interface 43, a region of interest so as to include point groups having the different color on the scatter diagram, for example.

Similarly, if the operator sets the region R211 to the region R511 on the monochromatic X-ray image, the display control function 445 displays, on the scatter diagram, point groups corresponding to the set regions R211 to R511 in different colors. The operator is able to set, on the scatter diagram, the region of interest R21 to the region of interest R51 corresponding to the region R211 to the region R511 by setting a plurality of regions of interest so as to include corresponding point groups having the respective different colors on the scatter diagram.

As described above, if the operator sets the region of interest on the scatter diagram, the analysis function 444 identifies the inside of the set region of interest as an approximate position of the target tissue, for which the contrast is to be enhanced, on the scatter diagram. Here, the analysis function 444 is able to store, in the memory 41, the position and the shape of the region of interest that is set by the operator on the scatter diagram. The position of the region of interest on the scatter diagram set by the operator indicates the mixture ratio of the reference materials of the target tissue for which the contrast is to be enhanced. Therefore, because the mixture ratio of the reference materials in the same target tissue does not change not only in a single subject, but also between different subjects, it is highly likely that the approximate position of the target tissue on the scatter diagram is an identical position.

Therefore, the analysis function 444 stores, in the memory 41, the position and the shape of the region of interest that is set on the scatter diagram by the operator, and, in a subsequent process of setting a region of interest, the analysis function 444 identifies, on the scatter diagram, the position of the region of interest stored in the memory 41 as an approximate position of the target tissue for which the contrast is to be enhanced, so that it is possible to reduce time and effort for the operator to set the region of interest and it is possible to generate an accurate analysis image even when the operator performs any kind of analysis. For example, when the analysis function 444 re-generates an analysis image of the same subject as a subject for whom information on the position and the shape of the region of interest has been stored in the memory 41, the analysis function 444 arranges a region of interest having the same shape as stored in the memory 41 at the stored position, and identifies the inside of the arranged region of interest as an approximate position of the target tissue on the scatter diagram.

Meanwhile, when the analysis function 444 uses the stored information on the position of the region of interest, the analysis function 444 may accept adjustment of the region of interest. In this case, if a process of identifying, on the scatter diagram, the approximate position of the target tissue for which the contrast is to be enhanced is started, the display control function 445 displays a region of interest with the stored shape at a position corresponding to the stored position on the scatter diagram. Further, the display control function 445 displays the monochromatic X-ray image in which a color of the pixel groups in the image corresponding to the point groups included in the arranged region of interest is changed.

The operator adjusts the shape and the position of the region of interest on the scatter diagram by operating the input interface 43 while referring to the region of interest on the displayed scatter diagram and the monochromatic X-ray image. The analysis function 444 identifies the inside of the adjusted region of interest as the approximate position of the target tissue on the scatter diagram. For example, when the analysis function 444 generates an analysis image of a subject different from the subject for whom the information on the position and the shape of the region of interest has been stored in the memory 41, the analysis function 444 accepts adjustment of the region of interest as described above.

Meanwhile, the analysis function 444 is able to store the above-described region of interest for each of subjects or for each of operators. In this case, for example, the analysis function 444 acquires subject information or operator information, and stores the acquired information and the information on the region of interest in an associated manner. Further, the analysis function 444 may also be able to store the set region of interest for each of target tissues. In this case, the analysis function 444 acquires information on the target tissue for which the region of interest has been set, and stores the acquired information on the target tissue and the information on the region of interest in an associated manner in the memory 41. Meanwhile, the information on the target tissue is input by, for example, the operator.

Furthermore, the analysis function 444 may appropriately update the information on the region of interest stored in the memory 41. For example, the analysis function 444 may update the region of interest stored in the memory 41 with an adjusted region every time the stored region of interest is adjusted as described above. Moreover, if the region of interest is set for each of target tissues, the analysis function 444 further sets a new region of interest by using the information on the region of interest stored in the memory 41 and information on the newly-set region of interest every time a region of interest for which information on the target tissue is to be acquired is newly set, for example. Then, the analysis function 444 updates the region of interest corresponding to the target tissue stored in the memory 41 with the newly-set region of interest.

As described above, if the region of interest is set as an approximate position of the target tissue on the scatter diagram, the analysis function 444 sets different weights for point groups included in the set region of interest and reflects the weights in the luminance values of the CT image, to thereby change the contrast of the target tissue. For example, the analysis function 444 performs weighting based on the center of gravity with respect to the point groups included in the region of interest, and adds contrast to the target tissue.

Figure 5:
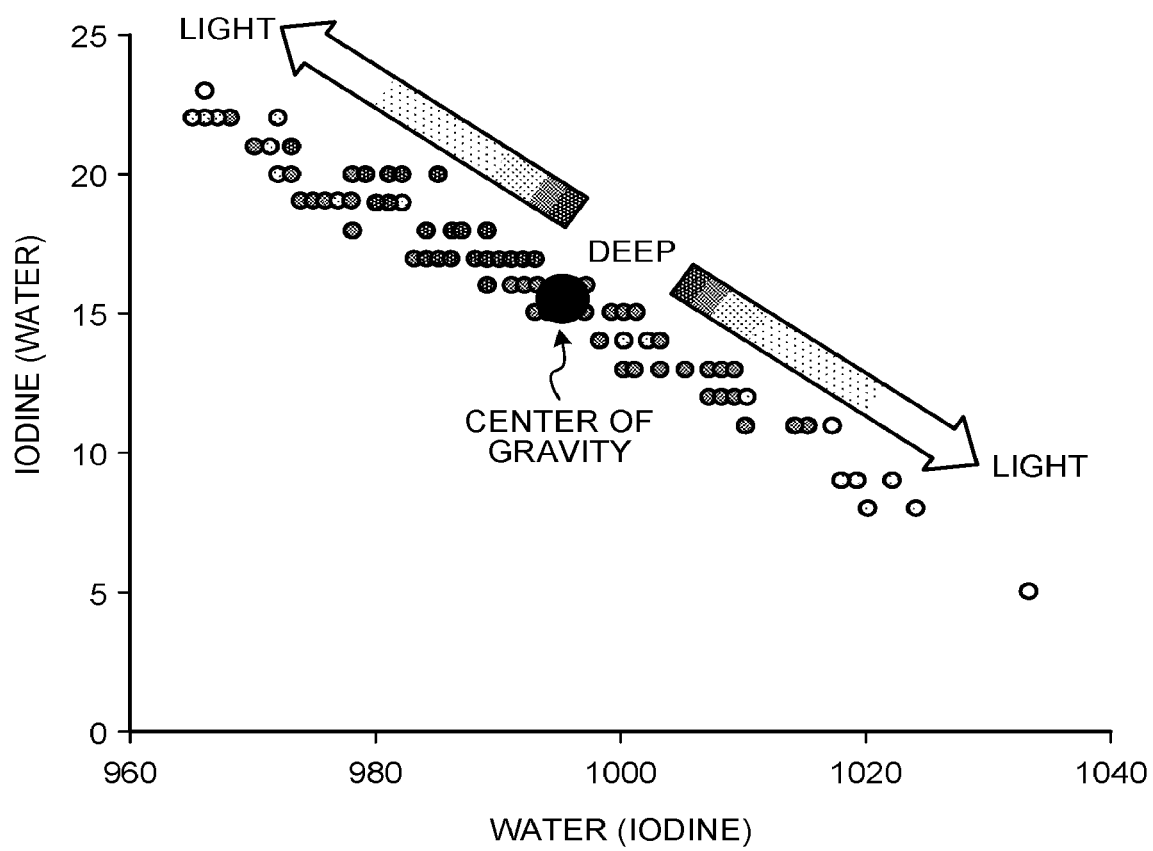
FIG. 5 is a diagram for explaining an example of weighting performed by an analysis function according to the first embodiment.

FIG. 5 is a diagram for explaining an example of weighting performed by the analysis function 444 according to the first embodiment. FIG. 5 is an enlarged view of the region of interest R51 that is set in the scatter diagram illustrated in FIG. 4. That is, point groups illustrated in FIG. 5 are point groups included in the region of interest R51. For example, as illustrated in FIG. 5, the analysis function 444 performs weighting such that the density at the center of gravity of the point groups is increased and the density is reduced with an increase in the distance from the center of gravity.

As described above, the scatter diagram represents the mixture ratio of the reference materials, and points indicating pixels of an identical tissue (identical substance) are expected to be plotted at substantially the same coordinate on the scatter diagram; however, due to the influence of noise or the like, even the points of the pixels of the identical tissue (identical substance) are distributed. However, even if the points are distributed due to the influence of noise or the like, it is assumed that the points indicating the pixels of the identical tissue (identical substance) are distributed in a concentrated manner at around approximately the same coordinate on the scatter diagram. As one example, in a region of interest in which a predetermined substance included in brain parenchyma is set as the target tissue, it is assumed that points representing pixels of the predetermined substance are distributed in a concentrated manner at around approximately the same coordinate on the scatter diagram.

Therefore, the analysis function 444 of the present disclosure extracts the center of gravity of the point groups included in the region of interest, and performs weighting centering on the extracting center of gravity. For example, the analysis function 444 counts the number of points for each of the coordinates on the scatter diagram by adopting the point groups included in the region of interest as a target. Then, the analysis function 444 extracts the coordinate at which the number of points counted for each of the coordinates is the largest as the center of gravity of the point groups included in the region of interest. Further, the analysis function 444 sets weights depending on distances from the extracted coordinate. For example, the analysis function 444 sets the weights such that the weights are reduced with an increase in the distance from the extracted coordinate.

Then, the analysis function 444 generates the analysis image by reflecting the set weights in the pixel values of the CT image. For example, the analysis function 444 performs weighting such that a pixel corresponding to a point of the coordinate of the center of gravity has the highest luminance (lowest luminance) and lower luminance (higher luminance) is set with an increase in the distance from the center of gravity, so that it is possible to display the pixels of the identical tissue (identical substance) in an enhanced manner among the pixels corresponding to the point groups included in the region of interest.

For example, the analysis function 444 extracts the center of gravity from point groups in a region of interest in which a predetermined material (for example, a material constituting gray matter) included in brain parenchyma is set as a target tissue, and performs weighting such that a pixel corresponding to a point of the coordinate of the extracted center of gravity has the highest luminance and the luminance is reduced with an increase in a distance from the center of gravity. Accordingly, the analysis function 444 is able to generate, for example, a CT image (analysis image) in which gray matter in brain parenchyma is enhanced and contrast with respect to white matter is clarified, or an analysis image in which contrast between a normal tissue and a lesion tissue in gray matter is clarified. That is, by selectively enhancing the contrast of an identical tissue (tissue with same material composition) in a certain tissue, the analysis function 444 is able to generate the analysis image in which the tissue and other tissues are displayed in a distinguishing manner. Meanwhile, the luminance value of the pixel corresponding to the point of the coordinate of the center of gravity and a degree of reduction of the luminance (gradient of luminance) corresponding to the distance from the center of gravity can be arbitrarily set in advance.

Here, it is possible to use any CT image for generating the analysis image. For example, the analysis function 444 is able to generate the analysis image by using a monochromatic X-ray image, a multicolor X-ray image, a reference material image, or the like at predetermined energy. Meanwhile, the CT image used for the analysis image may be determined based on, for example, diagnosis contents.

Further, the analysis function 444 may be able to extract the center of gravity for each of the regions of interest set on the scatter diagram, and perform weighting based on each of the extracted centers of gravity. For example, the analysis function 444 extracts the center of gravity for each of the region of interest R11 to the region of interest R51 illustrated in FIG. 4, and performs weighting for each of the extracted centers of gravity. Then, the analysis function 444 generates the analysis image by reflecting the set weight to each of pixel values of corresponding pixels in the CT image.

In this case, the analysis function 444 sets different weights for the respective regions of interest. That is, the analysis function 444 sets different weights for the centers of gravity extracted in the respective regions of interest. As one example, when performing weighting for each of the region of interest R11 to the region of interest R51, the analysis function 444 sets different weights for the centers of gravity extracted in the respective regions of interest such that luminance values of pixels corresponding to the coordinates of the centers of gravity in the respective regions of interest become different from one another.

Figure 6:
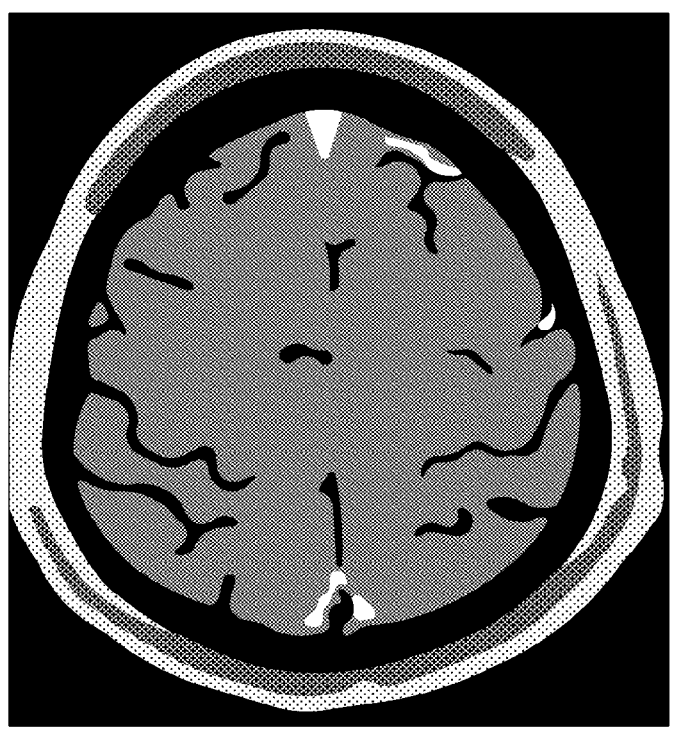
FIG. 6 is a diagram illustrating an example of an analysis image according to the first embodiment.

FIG. 6 is a diagram illustrating an example of the analysis image according to the first embodiment. For example, the analysis function 444 sets different weights for the centers of gravity extracted in the respective regions of interest such that the luminance values of the pixels corresponding to the coordinates of the centers of the gravity in the respective regions of interest become different from one another, and corrects the pixel values of the corresponding pixels on the CT image on the basis of the weights, so that the analysis image in which the tissue resolution is improved as illustrated in FIG. 6 is generated. That is, through the process as described above, the analysis function 444 is able to generate the CT image in which the contrast is enhanced with respect to fat, a muscle, a tumor, water, a bone, and the like. The analysis image can be generated based on the CT image that is captured by plain CT scan in which a contrast agent is not used. In other words, the X-ray CT apparatus 1 according to the present embodiment is able to generate, through the imaging by plain CT scan, the analysis image that is similar to an MRI image in which tissue resolution is increased.

Meanwhile, when the plurality of regions of interest is set in the scatter diagram, in some cases, it may be difficult to set different luminance values of pixels corresponding to the coordinates of the centers of gravity of the respective regions of interest. Therefore, the X-ray CT apparatus 1 may include a GUI that allows the operator to freely change the weight of each of the regions of interest. In this case, for example, the display control function 445 causes the display 42 to display a GUI that can independently change the weights of the region of interest R11 to the region of interest R51, in addition to displaying the analysis image generated by the analysis function 444. The operator changes the weight of each of the region of interest R11 to the region of interest R51 by operating the GUI on the display 42 via the input interface 43. Here, the change of the weight by the operator includes a change of the luminance value applied to the pixel of the coordinate of the center of gravity and the luminance gradient that varies depending on the distance from the center of gravity.

The analysis function 444 generates the analysis image in which the luminance values are changed in accordance with the weight change operation that is performed in each of the regions of interest via the input interface 43. The display control function 445 continually updates the analysis image displayed on the display 42 every time the analysis function 444 generates the analysis image. For example, the operator is able to display a desired analysis image by operating the GUI for changing the weights while observing the analysis image displayed on the display 42. Therefore, the X-ray CT apparatus 1 is able to display the analysis image while distinguishing regions, such as brain parenchyma and water, which overlap with each other on the image.

Meanwhile, a display mode of the analysis image is not limited to the example as illustrated in FIG. 6, but various other modes may be adopted. For example, as illustrated in FIG. 3 and FIG. 4, the display control function 445 is able to display the analysis image side by side with the scatter diagram and the reference material image. Here, if the scatter diagram is displayed side by side, the display control function 445 is able to further display a GUI for receiving operation of changing the regions of interest set in the scatter diagram. That is, the operator is able to arbitrarily change the regions of interest in the scatter diagram or the weight of each of the regions of interest while referring to the analysis image.

Further, for example, it may be possible to generate an analysis image for each of the regions of interest and display the plurality of generated analysis images side by side, instead of reflecting, in a single analysis image, the weights that are set for the respective regions of interest as illustrated in FIG. 6. As one example, the analysis function 444 generates an analysis image in which the weight is reflected in pixel values of pixels corresponding to point groups included in the region of interest R11, an analysis image in which the weight is reflected in pixel values of pixels corresponding to point groups included in the region of interest R21, an analysis image in which the weight is reflected in pixel values of pixels corresponding to point groups included in the region of interest R31, an analysis image in which the weight is reflected in pixel values of pixels corresponding to the point group included in the region of interest R41, and an analysis image in which the weight is reflected in pixel values of pixels corresponding to the point group included in the region of interest R51. The display control function 445 displays the generated five analysis images side by side. Meanwhile, the display control function 445 is able to cause the display 42 to display a GUI for changing the weight of each of the regions of interest with respect to the analysis images. With this configuration, the X-ray CT apparatus 1 is able to generate and display the analysis image in which, for example, each of tissues (substances), such as water, fat, a muscle, and a bone, is enhanced.

Figure 7:
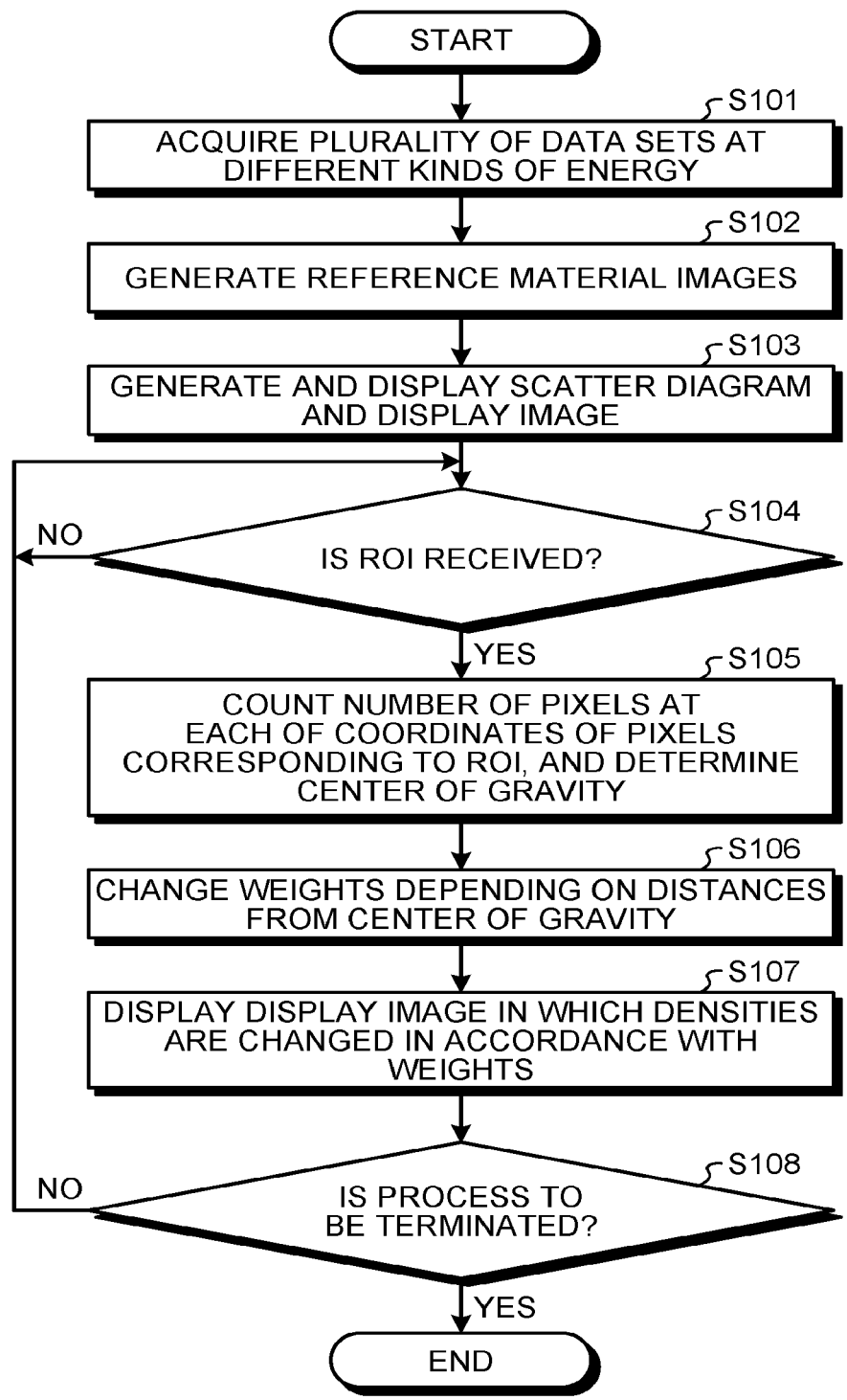
FIG. 7 is a flowchart for explaining the flow of a process performed by the X-ray CT apparatus according to the first embodiment.

Next, an example of the flow of a process performed by the X-ray CT apparatus 1 will be described with reference to FIG. 7. FIG. 7 is a flowchart for explaining the flow of the process performed by the X-ray CT apparatus 1 according to the first embodiment. In FIG. 7, a case will be described in which the operator sets a region of interest (ROI).

Step S101 is a step corresponding to the scan control function 441. Step S102 is a step corresponding to the image reconstruction function 443. Step S103 is a step corresponding to the image reconstruction function 443 and the analysis function 444. Step S104 to Step S106 and Step S108 are steps corresponding to the analysis function 444. Step S107 is a step corresponding to the display control function 445.

First, the processing circuitry 44 acquires a plurality of data sets at different kinds of energy (Step S101). Subsequently, the processing circuitry 44 generates reference material images (Step S102), and generates and displays a scatter diagram and a display image (Step S103). Thereafter, the processing circuitry 44 determines whether a ROI is received (Step S104).

If setting of the ROI is received (Yes at Step S104), the processing circuitry 44 counts the number of pixels at each of coordinates of pixels corresponding to the ROI, and sets the center of gravity (Step S105). Meanwhile, the processing circuitry 44 is in a standby state until receiving the setting of the ROI (No at Step S104).

If the center of gravity is set at Step S105, the processing circuitry 44 changes weights depending on distances from the center of gravity (Step S106), and displays a display image (analysis image) in which densities are changed in accordance with the changed weights (Step S107). Thereafter, the processing circuitry 44 determines whether to terminate the process (Step S108), and if receiving termination operation (Yes at Step S108), the processing circuitry 44 terminates the process. Meanwhile, the processing circuitry 44 is in the standby state until receiving the termination operation (No at Step S108).

As described above, according to the first embodiment, by performing scanning using X-rays, the scan control function 441 acquires the first data set corresponding to the first X-ray energy and the second data set corresponding to the second X-ray energy different from the first X-ray energy with respect to a region including a part of the subject. The analysis function 444 generates the scatter diagram representing the contained amount of each of the reference materials at each of positions in the region on the basis of the first data set and the second data set, sets weights for at least a part of the scatter diagram, and generates the analysis image based on the contained amounts and the weights. Therefore, the X-ray CT apparatus 1 according to the first embodiment is able to display the analysis image in which an identical tissue (substance) is imaged in a weighted manner, and is able to generate the CT image in which the identical tissue (substance) is enhanced and the tissue resolution is improved.

Furthermore, as described above, according to the first embodiment, the analysis function 444 sets different weights for a plurality of regions of interest that are set in the scatter diagram. Therefore, the X-ray CT apparatus 1 according to the first embodiment is able to set the contrast for each of tissues and generate the CT image in which the tissue resolution is improved.

Moreover, as described above, according to the first embodiment, the input interface 43 receives change operation of changing the regions of interest. The analysis function 444 sets a weight for a region of interest subjected to the change operation received by the input interface 43. Therefore, the X-ray CT apparatus 1 according to the first embodiment is able to appropriately adjust pixels included in a target tissue, and therefore is able to generate the CT image that can more easily be observed.

Furthermore, as described above, according to the first embodiment, the memory 41 stores therein information on the regions of interest set in the scatter diagram. The analysis function 444 sets regions of interest in a newly-generated scatter diagram on the basis of the information on the regions of interest stored in the memory 41. Therefore, the X-ray CT apparatus 1 according to the first embodiment is able to save time and effort for setting the regions of interest, and generate the CT image that can easily be observed even when operated by any operator.

Moreover, as described above, according to the first embodiment, with respect to a distribution of the contained amounts indicated by the scatter diagram, the analysis function 444 extracts the center of gravity of the region of interest set in the scatter diagram, and sets weights depending on distances from the extracted center of gravity. Therefore, the X-ray CT apparatus 1 according to the first embodiment is able to easily enhance the identical tissue (substance).

Furthermore, as described above, according to the first embodiment, the analysis function 444 sets the weights such that the weights are reduced with an increase in the distance from the center of gravity. Therefore, the X-ray CT apparatus 1 according to the first embodiment is able to enhance the identical tissue (substance) with high accuracy.

Moreover, as described above, according to the first embodiment, the input interface 43 receives the change operation of changing the weights. The analysis function 444 generates the analysis image on the basis of the weights and the contained amounts after execution of the change operation received by the input interface 43. Therefore, the X-ray CT apparatus 1 according to the first embodiment is able to adjust the contrast for each of tissues (substances), and provide the CT image that can more easily be observed.

Furthermore, as described above, according to the first embodiment, the analysis function 444 estimates the contained amount of each of the reference materials for each of positions in the region, and generates the analysis image by correcting pixel values, which correspond to at least a part of the scatter diagram and which are based on the contained amounts that are estimated for at least a part of the region, by using the weights. Therefore, the X-ray CT apparatus 1 according to the first embodiment is able to adjust the contrast for each of tissues (substances).

Second Embodiment

In the first embodiment as described above, a case has been described in which the weight is added to each of the regions of interest. In a second embodiment, a case will be described in which a weight is added to each of positions of a region of interest. The X-ray CT apparatus 1 according to the second embodiment has the same configuration as the X-ray CT apparatus 1 illustrated in FIG. 2, but the analysis function 444 performs a partly-different process. In the following, components having the same configurations as those of the first embodiment will be denoted by the same reference symbols as illustrated in FIG. 2, and explanation thereof will be omitted.

Figure 8:
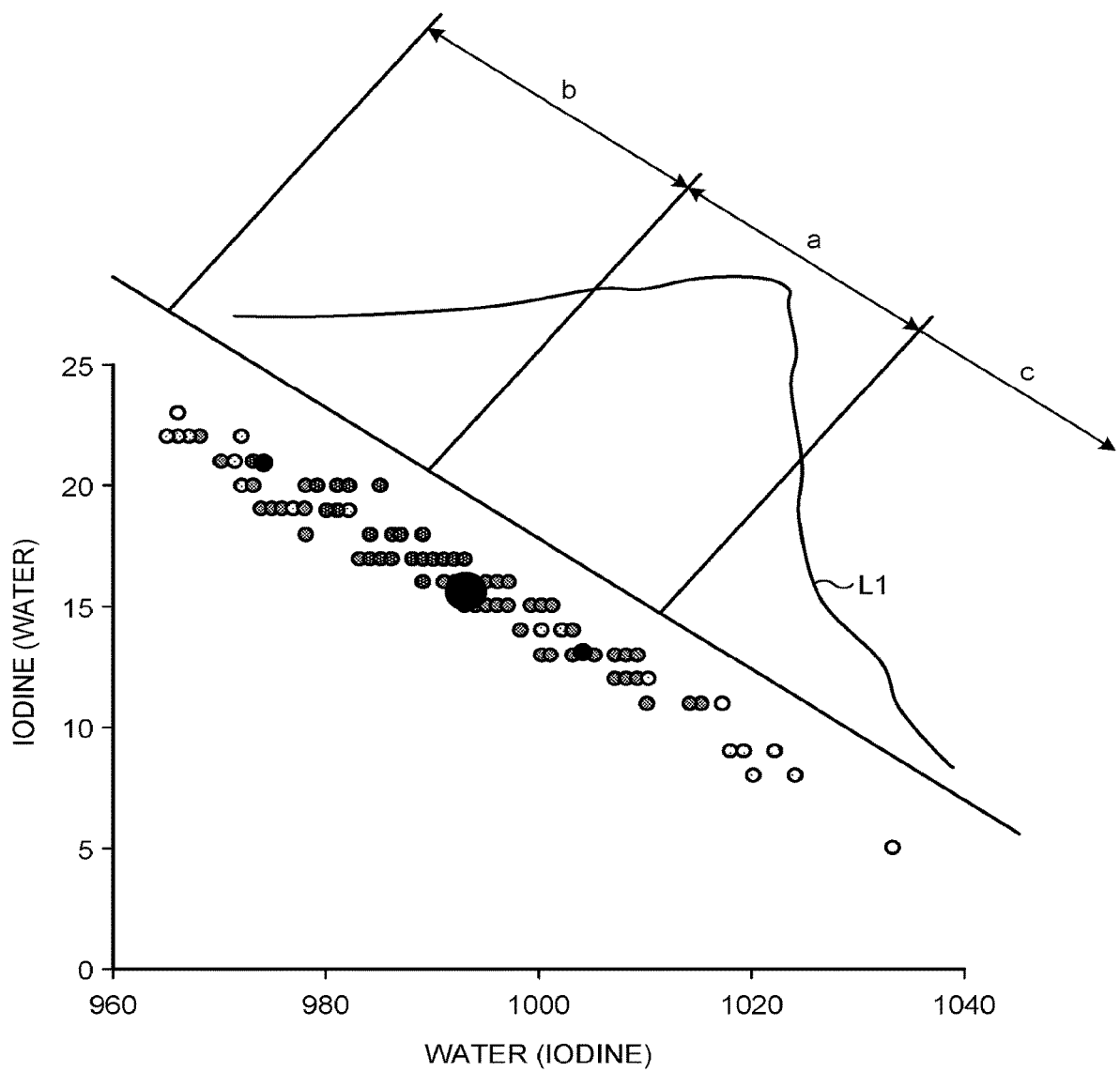
FIG. 8 is a diagram for explaining an example of weighting according to a second embodiment.

The analysis function 444 according to the second embodiment sets different weights for a plurality of positions in a region of interest set in the scatter diagram. For example, the analysis function 444 sets the same weight for a range for which a distance from the center of gravity is smaller than a threshold in a distribution of the contained amounts. FIG. 8 is a diagram for explaining an example of weighting according to the second embodiment. In FIG. 8, a case is illustrated in which a weight is added for each of positions in the scatter diagram illustrated in FIG. 5 (the enlarged view of the region of interest R51). Further, in FIG. 8, a graph adjacent to a distribution of point groups is a histogram, in which the vertical axis represents the number of points and the horizontal axis represents positions of the points.

For example, the analysis function 444 sets ranges in the scatter diagram in accordance with the distribution of the point groups in the scatter diagram, and adds a weight for each of the set ranges. As one example, as illustrated in FIG. 8, the analysis function 444 sets a range a including a peak position in the histogram, a range b, and a range c in the scatter diagram, and sets different weights for the respective set ranges.

For example, the analysis function 444 adds the same weight to point groups included in the range a, and adds weights to points groups included in the range b and the range c such that the weights are reduced from point groups located at the side of the range a. Accordingly, in an analysis image generated by the analysis function 444, pixels corresponding to the point groups included in the range a are enhanced. As described above, in the scatter diagram, in some case, positions corresponding to the identical tissue (substance) on the scatter diagram may be deviated due to the influence of noise or the like. Through the weighting performed by the analysis function 444 as described above, it is possible to represent, by the same luminance value, pixels of the identical tissue (substance) for which the positions of points are deviated due to the influence of noise or the like; consequently, it is possible to provide an observation image in which noise is reduced.

Furthermore, the analysis function 444 is able to extract centers of gravity from the point groups included in the range a, the point groups included in the range b, and the point groups included in the range c, and perform weighting based on the extracted centers of gravity. As one example, the analysis function 444 counts the number of point groups included in the range a at each of positions, and extracts a position of the center of gravity. Then, the analysis function 444 performs weighting for the point groups included in the range a such that a density of the extracted center of gravity is increased and the density is reduced with an increase in a distance from the center of gravity. Similarly, the analysis function 444 counts the number of point groups included in the range b at each of positions, and extracts a position of the center of gravity. Then, the analysis function 444 performs weighting for the point groups included in the range b such that a density of the extracted center of gravity is increased and the density is reduced with an increase in a distance from the center of gravity. Furthermore, the analysis function 444 counts the number of point groups included in the range c at each of positions, and extracts a position of the center of gravity. Then, the analysis function 444 performs weighting for the point groups included in the range c such that a density of the extracted center of gravity is increased and the density is reduced with an increase in a distance from the center of gravity.

Figure 9:
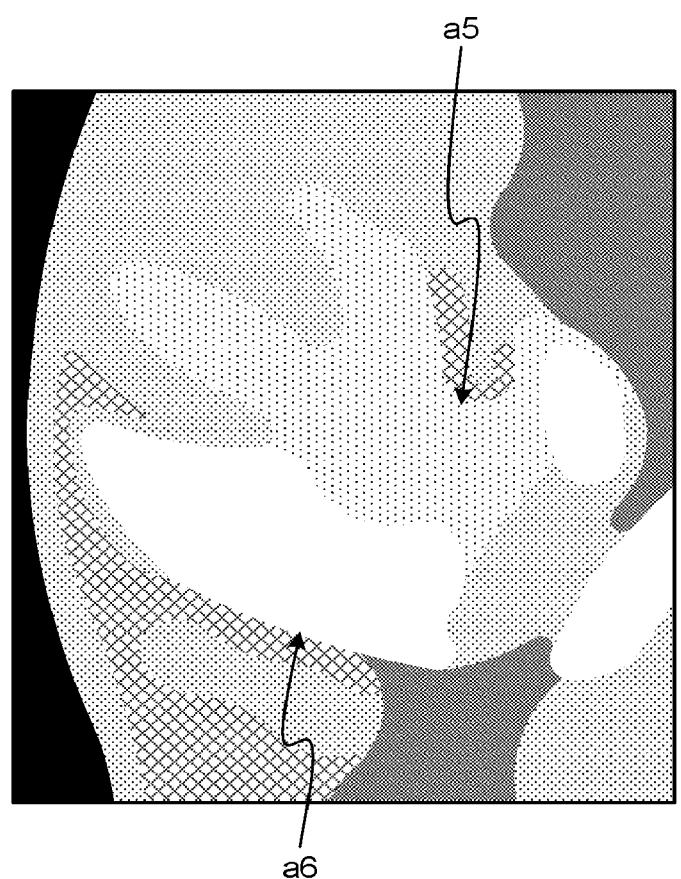
FIG. 9 is a diagram illustrating an example of an analysis image according to the second embodiment.

In this manner, the analysis function 444 is able to set fine contrast for a tissue (substance) by adding different weights to respective ranges in the region of interest. For example, by performing the above-described weighting in a region of interest in which a predetermined substance included in an edema of brain parenchyma is adopted as a target tissue, the analysis function 444 is able to generate an analysis image as illustrated in FIG. 9 in which a full edema region indicated by an arrow a6 and an edema region in which brain parenchyma remains as indicated by an arrow a5 are clearly distinguished and represented by different luminance values. That is, even when tissues include the same substance, if compositions of substances contained in the tissues are different, point groups are formed at different positions in the region of interest. The analysis function 444 according to the present embodiment is able to enhance each of the above-described tissues in a distinguishing manner. Meanwhile, FIG. 9 is a diagram illustrating an example of the analysis image according to the second embodiment.

As described above, according to the second embodiment, the analysis function 444 sets different weights for a plurality of positions in the region of interest that is set in the scatter diagram. Therefore, the X-ray CT apparatus 1 according to the second embodiment is able to add fine contrast to a tissue (substance).

Furthermore, according to the second embodiment, the analysis function 444 sets the same weight to a range for which the distance from the center of gravity is smaller than the threshold in the distribution of the contained amount. Therefore, the X-ray CT apparatus 1 according to the second embodiment is able to provide the CT image in which noise is reduced.

Third Embodiment

In a third embodiment, a case will be described in which noise in a scatter diagram (image) is identified and the identified noise is reduced. The X-ray CT apparatus 1 according to the third embodiment has the same configuration as the X-ray CT apparatus 1 illustrated in FIG. 2, but the analysis function 444 performs a partly-different process. In the following, components having the same configurations as those of the first embodiment will be denoted by the same reference symbols as illustrated in FIG. 2, and explanation thereof will be omitted.

The analysis function 444 according to the third embodiment identifies noise in a scatter diagram, and generates an analysis image in which the identified noise is reduced. For example, the analysis function 444 identifies, as noise, a point whose appearance frequency is smaller than a threshold in the scatter diagram. As one example, the analysis function 444 counts the number of points that are distributed at the same coordinate in point groups in the scatter diagram, and identifies, as noise, a point at the coordinate at which the counted value is smaller than a threshold. Then, the analysis function 444 corrects the luminance value of the pixel corresponding to the point that is identified as noise to, for example, the same value as the luminance value of the pixel corresponding to the point located at the center of gravity, to thereby reduce noise in the analysis image.

While the example has been described above in which noise is reduced by correcting the luminance value of the pixel corresponding to the point that is identified as noise to the same value as the luminance value of the pixel corresponding to the point located at the center of gravity. However, embodiments are not limited to the above-described example, and it may be possible to, for example, eliminate, from an analysis target, the point that is identified as noise, and eliminate the point from pixels to which weights are to be added.

Furthermore, in the above-described example, a case has been described in which noise is identified by using the scatter diagram. However, embodiments are not limited to this example, and it may be possible to identify noise from an image. In this case, the analysis function 444 identifies a pixel corresponding to noise in the image, for example. Then, the analysis function 444 may perform other noise reduction processes on the pixel that is identified as noise.

As described above, according to the third embodiment, the analysis function 444 identifies noise in the scatter diagram, and generates an analysis image in which the identified noise is reduced. Therefore, the X-ray CT apparatus 1 according to the third embodiment is able to generate the analysis image in which noise is reduced.

Furthermore, according to the third embodiment, the analysis function 444 identifies, as noise, a point whose appearance frequency is smaller than the threshold in the scatter diagram. Therefore, the X-ray CT apparatus 1 according to the third embodiment is able to easily identify noise from the scatter diagram.

Fourth Embodiment

In the above-described embodiments, a case has been described in which the luminance values in the analysis image are changed based on the weights. In a fourth embodiment, a case will be described in which a color image is formed based on weights. The X-ray CT apparatus 1 according to the fourth embodiment has the same configuration as the X-ray CT apparatus 1 illustrated in FIG. 2, but the analysis function 444 performs a partly-different process. In the following, components having the same configurations as those of the first embodiment will be denoted by the same reference symbols as illustrated in FIG. 2, and explanation thereof will be omitted.

Figure 10:
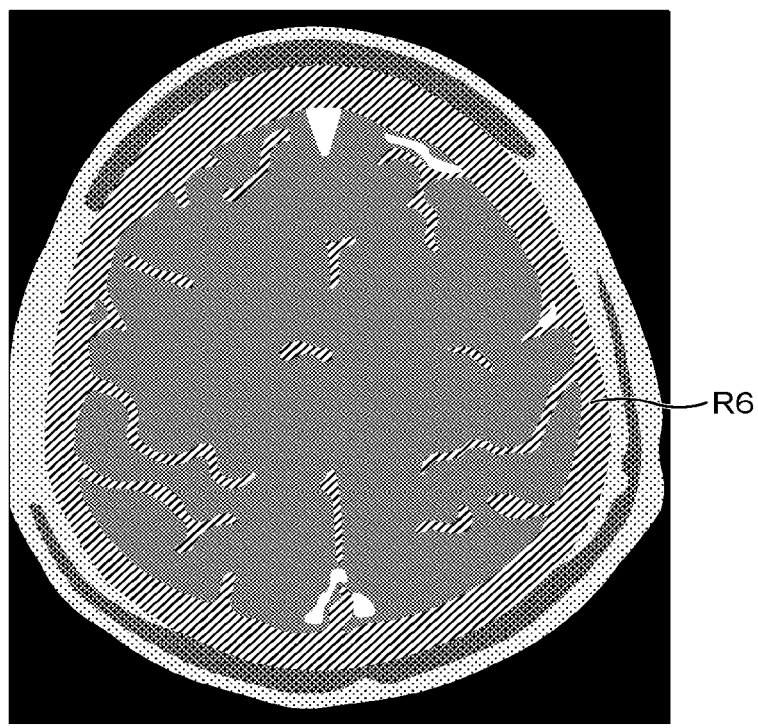
FIG. 10 is a diagram illustrating an example of an analysis image according to a fourth embodiment.

The analysis function 444 according to the fourth embodiment generates a color analysis image by adding colors corresponding to weights to corresponding pixels. For example, the analysis function 444 generates an analysis image in which a certain color is associated with each of the regions of interest and color densities are changed based on the weights. FIG. 10 is a diagram illustrating an example of the analysis image according to the fourth embodiment. In FIG. 10, a case is illustrated in which the analysis image illustrated in FIG. 6 is colored.

For example, the analysis function 444 generates a color image in which a predetermined color (for example, blue or the like) is associated with a region of interest corresponding to pixels of a region R6 (cerebrospinal fluid region) in FIG. 10 and color densities are changed in accordance with weights that are set based on point groups in the region of interest. That is, the analysis function 444 generates a color image in which the pixels included in the region R6 are colored in blue at different densities depending on the weights. The display control function 445 causes the display 42 to display the color image generated by the analysis function 444.

Here, it is possible to cause the analysis function 444 to generate a color image depending on selection of the region of interest. That is, every time the operator changes the region of interest via the input interface 43, the analysis function 444 generates a color image for the changed region of interest. Then, the display control function 445 causes the display 42 to display the generated color image. Therefore, the operator is able to observe the color image in which a desired tissue (substance) is colored.

Fifth Embodiment

While the first to the fourth embodiments have been described above, various different embodiments may be made in addition to the first to the fourth embodiments as described above.

In the above-described embodiments, the example has been described in which the high-energy projection data set and the low-energy projection data set that are obtained by Dual-Energy imaging has been described. However, embodiments are not limited to this example, and it may be possible to use projection data sets that correspond to three or more different kinds of energy and that are acquired by "Multi-Energy imaging" at three or more different tube voltages.

Furthermore, in the above-described embodiments, the example has been described in which the analysis image that is similar to an MRI image with high tissue resolution is generated by enhancing contrast of each of tissues. However, embodiments are not limited to this example, and it may be possible to generate, for example, a virtual contrast image. In this case, for example, by adding weights such that pixel groups corresponding to point groups that are included in a region of interest corresponding to a portion, such as a tumor or a vascular tissue, which is likely to be affected by a contrast agent have the highest luminance value, the analysis function 444 is able to generate a virtual contrast image using a CT image that is captured by plain CT scan.

Moreover, in the above-described embodiments, the example has been described in which the analysis image of brain is generated, but embodiments are not limited thereto, and it may be possible to generate analysis images of various other regions.

Furthermore, in the above-described embodiments, the example has been described in which weighting is performed centering on the center of gravity of the point groups. However, embodiments are not limited to this example, and it may be possible to perform weighting centering on a peak position in the distribution of the point groups.

Moreover, in the above-described embodiments, the example has been described in which data sets acquired by capturing images through plain CT scan are used. However, embodiments are not limited to this example, and it may be possible to use data sets acquired by capturing images through contrast enhanced CT examination.

Furthermore, in the above-described embodiments, the example has been described in which weighting is performed so as to enhance the contrast of each of tissues (substances). However, embodiments are not limited to this example, and it may be possible to perform weighting such that pixels corresponding to a predetermined tissue (substance) are not displayed. As one example, the analysis function 444 generates an analysis image in which a bone is hidden by performing weighting such that luminance values of point groups included in the region of interest corresponding to the bone are set to "0".

Moreover, in the above-described embodiments, the example has been described in which the scatter diagram representing the contained amount of each of the reference materials is generated. However, embodiments are not limited to this example, and it may be possible to extract an identical tissue (identical substance) by using a mixture ratio of the reference materials based on the contained amounts of the reference materials, without generating the scatter diagram. In this case, the analysis function 444 estimates the contained amount of each of the reference materials at each of positions in a region on the basis of the first data set and the second data set, sets weights for at least a part of the region, and generates an analysis image based on the contained amounts and the weights.

Specifically, the analysis function 444 estimates abundance ratios among a plurality of reference materials for each of pixels on the basis of a plurality of data sets corresponding to different kinds of energy. Then, the analysis function 444 generates an analysis image based on the abundance ratios at each of the pixels without generating the scatter diagram. That is, the analysis function 444 generates the analysis image by performing a process using only numerical values. For example, the analysis function 444 estimates each of an abundance ratio of iodine to water and an abundance ratio of water to iodine for each of pixels of a region that is captured by Dual Energy imaging. Then, the analysis function 444 classifies the pixels into groups based on the estimated abundance ratios, sets weights among the groups and inside the groups, and generates an analysis image in which a luminance value of each of the pixels is converted to a luminance value in which the weight is reflected.

FIG. 11 is a schematic diagram for explaining a process performed by the analysis function 444 according to a fifth embodiment. An upper figure in FIG. 11 indicates each of pixels in image data. That is, (1, 1), (1, 2), (1, 3), and the like indicate coordinates of the respective pixels in the image data. While the pixels are distinguished from one another by the coordinates in FIG. 11, it may be possible to distinguish among the pixels by using only numbers.

For example, as illustrated in a middle figure in FIG. 11, the analysis function 444 estimates the abundance ratio of iodine to water "Iodine (Water)" and the abundance ratio of water to iodine "Water (Iodine)" for each of the pixels on the basis of a relationship between pixel values of a multicolor X-ray image corresponding to high energy and pixels values of a multicolor X-ray image corresponding to low energy, where the multicolor X-ray images are generated by the image reconstruction function 443. As one example, the analysis function 444 estimates "Iodine (Water): 10, Water (Iodine): 815" with respect to the pixel (1, 1).

After estimating the abundance ratio of iodine to water and the abundance ratio of water to iodine with respect to all of the pixels as described above, the analysis function 444 classifies the pixels into groups based on the estimated abundance ratios. For example, the analysis function 444 classifies the pixels into groups based on similarities of the abundance ratios. As a method used for determination of the similarities, any known method is applicable.

As one example, the analysis function 444 classifies pixels corresponding to "Iodine (Water): 10, Water (Iodine): 815", "Iodine (Water): 13, Water (Iodine): 822", "Iodine (Water): 11, Water (Iodine): 811", . . . "Iodine (Water): 13, Water (Iodine): 772", "Iodine (Water): 13, Water (Iodine): 822" . . . among all of the pixels into a group A. Further, the analysis function 444 classifies pixels corresponding to and similar to "Iodine (Water): 60, Water (Iodine): 1022" into a group B, and classifies pixels corresponding to and similar to "Iodine (Water): 255, Water (Iodine): 1506" into a group C. In this manner, the analysis function 444 classifies the pixels into the groups based on the contained amounts of the reference materials.

Here, each of the groups corresponds to one of tissues (substance), such as water, fat, a muscle, and a bone. That is, the groups are changed depending on tissues (substance) to be distinguished. In other words, ranges of the abundance ratios of the reference materials are set for each of tissues (substances) to be distinguished (for example, in a case of fat, a range of Iodine (Water) is a to b and a range of Water (Iodine) is c to d). Then, grouping is changed depending on a tissue (substance) that is to be adopted as a target when an analysis image is generated.

In this manner, when the pixels are classified into groups, the analysis function 444 sets weights among the groups and inside the groups, and generates an analysis image in which the luminance value of each of the pixels is changed to a luminance value in which the weight is reflected. For example, by setting different weights for the groups A, the group B, and the group C, the analysis function 444 is able to generate an analysis image in which contrast of tissues (substances), such as fat, a muscle, a tumor, water, and a bone, is enhanced.

Furthermore, by setting different weights for the respective pixels in the group, the analysis function 444 is able to generate an analysis image in which noise is reduced and fine contrast is added in a single tissue. For example, the analysis function 444 sets different ratios depending on appearance frequencies of the abundance ratios. As one example, the analysis function 444 sets different weights to pixels corresponding to "Iodine (Water): 13, Water (Iodine): 822" for which the appearance frequencies are high and other pixels for which the appearance frequencies are low in the group A. Consequently, it is possible to reduce noise and add fine contrast in a tissue corresponding to the group A.

Figure 12:
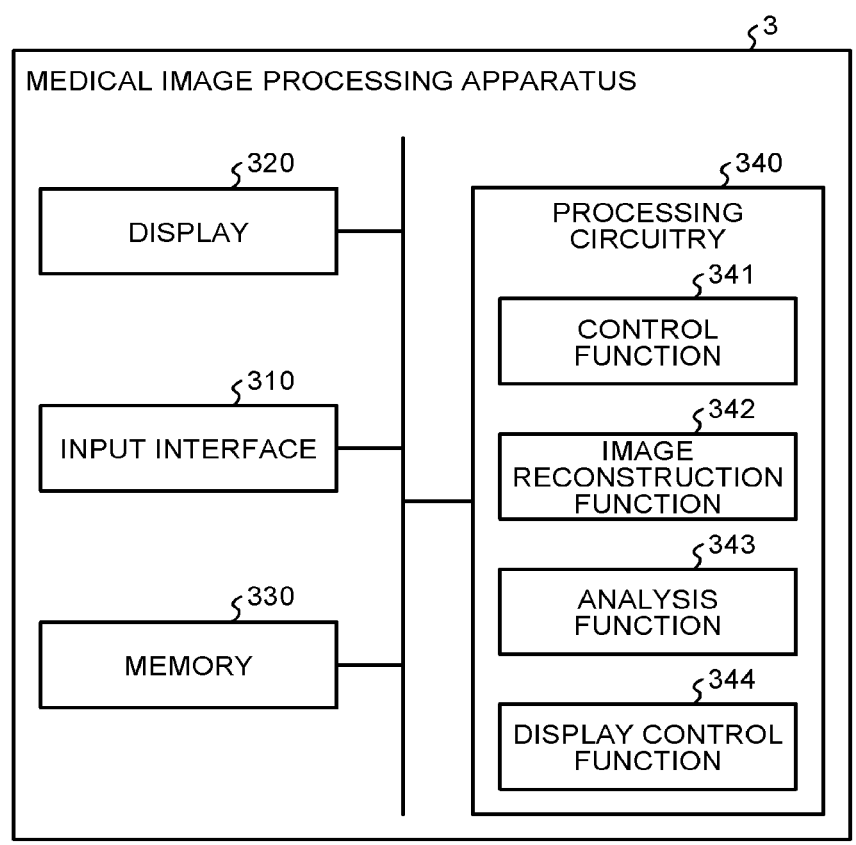
FIG. 12 is a diagram illustrating a configuration example of a medical image processing apparatus according to a fifth embodiment.

Moreover, in the above-described embodiments, a case has been described in which the X-ray CT apparatus 1 performs various processes. However, embodiments are not limited to this example, but it may be possible to cause, for example, the medical image processing apparatus 3 to perform various processes. FIG. 12 is a diagram illustrating an example of a configuration of the medical image processing apparatus 3 according to the fifth embodiment.

For example, as illustrated in FIG. 12, the medical image processing apparatus 3 includes an input interface 310, a display 320, a memory 330, and processing circuitry 340.

The input interface 310 is realized by a trackball, a switch button, a mouse, or a keyboard for performing various settings, a touch pad for performing input operation when an operation screen is touched, a touch screen in which a display screen and a touch pad are integrated, contactless input circuitry using an optical sensor, voice input circuitry, and the like.

The input interface 310 is connected to the processing circuitry 340, converts input operation received from an operator into an electrical signal, and outputs the electrical signal to the processing circuitry 340. Meanwhile, in the present disclosure, the input interface 310 is not limited to a device that includes a physical operating component, such as a mouse or a keyboard. For example, examples of the input interface include processing circuitry that receives an electrical signal corresponding to the input operation from an external input device that is provided separately from the device, and outputs the electrical signal to the processing circuitry 340.

The display 320 is connected to the processing circuitry 340, and displays various kinds of information and various kinds of image data output from the processing circuitry 340. For example, the display 320 is realized by a liquid crystal monitor, a cathode ray tube (CRT) monitor, or a touch panel. For example, the display 320 displays a graphical user interface (GUI) for receiving instructions from the operator, various display images, and various processing results (for example, the scatter diagram, the analysis image, and the like) obtained by the processing circuitry 340.

The memory 330 is connected to the processing circuitry 340 and stores therein various kinds of data. For example, the memory 330 is realized by a semiconductor memory device, such as a random access memory (RAM) or a flash memory, a hard disk, an optical disk, or the like. For example, the memory 330 stores therein CT image data received from the X-ray CT apparatus 1 or the image storage apparatus 2, information on the scatter diagram, the analysis image, and the region of interest, and the like. Further, the memory 330 stores therein a program corresponding to each of processing functions implemented by the processing circuitry 340.

The processing circuitry 340 controls each of the components included in the medical image processing apparatus 3 in accordance with input operation that is received from an operator via the input interface 310. For example, the processing circuitry 340 is realized by the processor. In the present embodiment, the processing circuitry 340 stores the CT image data output from the input interface 310 in the memory 330. Further, the processing circuitry 340 reads the CT image data from the memory 330, and displays the CT image data on the display 320.

Then, as illustrated in FIG. 12, the processing circuitry 340 implements a control function 341, an image reconstruction function 342, an analysis function 343, and a display control function 344. The control function 341 controls an entire medical image processing apparatus 3. The image reconstruction function 342 performs the same process as the process performed by the image reconstruction function 443 as described above. The analysis function 343 performs the same process as the process performed by the analysis function 444. The display control function 344 performs the same process as the process performed by the display control function 445.

In the above-described embodiments, independent processes performed by the X-ray CT apparatus 1 and the medical image processing apparatus 3 have been described. However, embodiments are not limited to this example, and the X-ray CT apparatus 1 and the medical image processing apparatus 3 may function as an X-ray CT system in cooperation with each other. In this case, the CT image data acquired by the X-ray CT apparatus 1 is transferred to the medical image processing apparatus 3, and the medical image processing apparatus 3 performs various processes.

The word "processor" used in the above description indicates a circuitry, such as a CPU, a graphics processing unit (GPU), an application specific integrated circuit (ASIC), a programmable logic device (for example, a simple programmable logic device (SPLD)), a complex programmable logic device (CPLD), and a field programmable gate array (FPGA). The processor implements the functions by reading programs stored in the memory 41 or a memory 53 and executing the programs.

In FIG. 2, a case has been described in which the single memory 41 stores therein programs corresponding to all of the processing functions. Further, in FIG. 12, a case has been described in which the single memory 330 stores therein programs corresponding to all of the processing functions. However, embodiments are not limited to this example. For example, it may be possible to arrange the plurality of memories 41 in a distributed manner, and cause the processing circuitry 44 to read a corresponding program from each of the memories 41. Furthermore, for example, it may be possible to arrange the plurality of memory circuitries 330 in a distributed manner, and cause the processing circuitry 340 to read a corresponding program from each of the memory circuitries 330. Moreover, it may be possible to directly incorporate the programs in circuitries in the processor instead of storing the programs in the memory 41 or the memory 330. In this case, the processor implements the function by reading the program incorporated in the circuitries and executing the program.

Furthermore, the processing circuitry 44 and the processing circuitry 340 may implement the functions by using a processor of an external apparatus that is connected via a network. For example, the processing circuitry 44 implements each of the functions illustrated in FIG. 2 by reading and executing a program corresponding to each of the functions from the memory 41 and using an external workstation or a cloud that is connected to the X-ray CT apparatus 1 via a network NW as a calculation resource. Furthermore, for example, the processing circuitry 340 implements each of the functions illustrated in FIG. 12 by reading and executing a program corresponding to each of the functions from the memory 330 and using an external workstation or a cloud that is connected to the medical image processing apparatus 3 via the network NW as a calculation resource.

The components of the apparatuses according to the above-described embodiments are functionally conceptual and need not necessarily be physically configured in the manner illustrated in the drawings. In other words, specific forms of distribution and integration of the apparatuses are not limited to those illustrated in the drawings, and all or part of the apparatuses may be functionally or physically distributed or integrated in arbitrary units depending on various loads or use conditions. Further, for each processing function performed by each device, all or any part of the processing functions may be implemented by a CPU and a program analyzed and executed by the CPU or may be implemented as hardware by wired logic.

Furthermore, the control method described in the embodiments above is realized by causing a computer, such as a personal computer or a workstation, to execute a control program that is prepared in advance. The control program may be distributed via a network, such as the Internet. Moreover, the control program may be recorded in a computer-readable recording medium, such as a hard disk, a flexible disk (FD), a compact disc-ROM (CD-ROM), a magneto-optical disk (MO), or a digital versatile disk (DVD), read from the recording medium by the computer, and executed by the computer.

According to at least one of the embodiments as described above, it is possible to provide a CT image in which tissue resolution is improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
   processing circuitry configured to
      acquire a first data set corresponding to first X-ray energy and a second data set corresponding to second X-ray energy different from the first X-ray energy, with respect to a region including a part of a subject by performing scanning using X-rays,
      generate a scatter diagram representing a contained amount of each of reference materials at each of positions in the region on the basis of the first data set and the second data set,
      set weights for at least a part of the scatter diagram, and generate an analysis image based on the contained amounts and the weights.

2. The X-ray CT apparatus according to claim 1, wherein the processing circuitry is configured to set different weights for a plurality of regions of interest that are set in the scatter diagram.

3. The X-ray CT apparatus according to claim 1, wherein the processing circuitry is configured to set different weights for a plurality of positions in a region of interest that is set in the scatter diagram.

4. The X-ray CT apparatus according to claim 2, further comprising:
   an input interface configured to receive change operation of changing the regions of interest, wherein the processing circuitry is configured to set a weight for a region of interest subjected to the change operation received by the input interface.

5. The X-ray CT apparatus according to claim 2, further comprising:
a memory configured to store therein information on the regions of interest that are set in the scatter diagram, wherein
the processing circuitry is configured to set a region of interest in a newly-generated scatter diagram on the basis of the information on the regions of interest stored in the memory.

6. The X-ray CT apparatus according to claim 2, wherein the processing circuitry is configured to extract a center of gravity in a region of interest set in the scatter diagram with respect to a distribution of the contained amounts indicated by the scatter diagram, and set weights depending on distances from the extracted center of gravity.

7. The X-ray CT apparatus according to claim 6, wherein the processing circuitry is configured to set the weights such that the weights are reduced with an increase in a distance from the center of gravity.

8. The X-ray CT apparatus according to claim 6, wherein the processing circuitry is configured to set the same weight for a range for which a distance from the center of gravity is smaller than a threshold in the distribution of the contained amounts.

9. The X-ray CT apparatus according to claim 1, further comprising:
an input interface for receiving change operation of changing the weights, wherein
the processing circuitry is configured to generate the analysis image on the basis of the weights subjected to the change operation received by the input interface and the contained amounts.

10. The X-ray CT apparatus according to claim 1, wherein the processing circuitry is configured to
estimate a contained amount of each of the reference materials for each of positions in the region, and
generate the analysis image by correcting pixel values, which correspond to at least a part of the scatter diagram and which are based on the contained amount that is estimated for at least a part of the region, by using the weights.

11. The X-ray CT apparatus according to claim 1, wherein the processing circuitry is configured to identify noise in the scatter diagram, and generate an analysis image in which the identified noise is reduced.

12. The X-ray CT apparatus according to claim 11, wherein the processing circuitry is configured to identify the contained amount for which appearance frequency is smaller than a threshold in the scatter diagram.

13. A medical image processing apparatus comprising:
processing circuitry configured to
collect a first data set corresponding to first X-ray energy and a second data set corresponding to second X-ray energy different from the first X-ray energy, the first data set and the second data set being collected with respect to a region including a part of a subject, by performing scanning using X-rays,
generate a scatter diagram representing a contained amount of each of reference materials at each of positions in the region on the basis of the first data set and the second data set,
set weights for at least a part of the scatter diagram, and generate an analysis image based on the contained amounts and the weights.

14. An X-ray CT system comprising:
an X-ray CT apparatus including processing circuitry configured to collect a first data set corresponding to first X-ray energy and a second data set corresponding to second X-ray energy different from the first X-ray energy, with respect to a region including a part of a subject by performing scanning using X-rays; and
a medical image processing apparatus including processing circuitry configured to generate a scatter diagram representing a contained amount of each of reference materials at each of positions in the region on the basis of the first data set and the second data set, set weights for at least a part of the scatter diagram, and generate an analysis image based on the contained amounts and the weights.

15. An X-ray CT apparatus comprising:
processing circuitry configured to
acquire a first data set corresponding to first X-ray energy and a second data set corresponding to second X-ray energy different from the first X-ray energy, with respect to a region including a part of a subject by performing scanning using X-rays,
estimate a contained amount of each of reference materials at each of positions in the region on the basis of the first data set and the second data set,
set weights for at least a part of the scatter diagram, and
generate an analysis image based on the contained amounts and the weights.

16. A medical image processing apparatus comprising:
processing circuitry configured to
collect, by performing scanning using X-rays, at least two data sets corresponding to at least two X-ray energies, the at least two data sets being collected with respect to a region including a part of a subject,
generate a scatter diagram representing contained amounts of each of plural reference materials at plural positions in the region based on the at least two data sets,
set weights for at least a part of the scatter diagram, and generate an analysis image based on the contained amounts and the weights.

17. The medical image processing apparatus according to claim 16, wherein the medical image processing apparatus is included in an X-ray CT apparatus.

18. The medical image processing apparatus according to claim 16, wherein the processing circuitry configured to collect the at least two data sets comprises processing circuitry configured to collect at least two X-ray CT images collected by performing CT scan in which a contrast agent is not used, and
wherein the processing circuitry configured to generate a scatter diagram comprises processing circuitry configured to generate the scatter diagram based on the at least two X-ray CT images.

19. The medical image processing apparatus according to claim 16, wherein the processing circuitry is further configured to set different weights for a plurality of regions of interest that are set in the scatter diagram.

20. The medical image processing apparatus according to claim 16, wherein the processing circuitry is further configured to set different weights for a plurality of positions in a region of interest that is set in the scatter diagram.

21. The medical image processing apparatus according to claim 19, further comprising an input interface configured to receive a change operation for changing the plurality of regions of interest, wherein the processing circuitry is configured to set a weight for a region of interest subjected to the change operation received by the input interface.

22. The medical image processing apparatus according to claim 16, further comprising an input interface for receiving a change operation for changing the weights,
wherein the processing circuitry is configured to generate the analysis image based on the weights subjected to the change operation received by the input interface and the contained amounts.

23. The medical image processing apparatus according to claim 16, wherein the processing circuitry is further configured to:
estimate the contained amounts of each of the plural reference materials for the plural positions in the region, and
generate the analysis image by correcting pixel values, which correspond to at least a part of the scatter diagram and which are based on the contained amounts that are estimated for at least a part of the region, by using the weights.

24. The medical image processing apparatus according to claim 16, wherein the processing circuitry is further configured to identify noise in the scatter diagram and generate an analysis image in which the identified noise is reduced.

* * * * *